(12) United States Patent
Yan et al.

(10) Patent No.: US 9,663,768 B2
(45) Date of Patent: May 30, 2017

(54) PRECURSOR-DIRECTED BIOSYNTHESIS OF 5-HYDROXYTRYPTOPHAN

(71) Applicant: UNIVERSITY OF GEORGIA RESEARCH FOUNDATION, INC., Athens, GA (US)

(72) Inventors: Yajun Yan, Bogart, GA (US); Xinxiao Sun, Athens, GA (US)

(73) Assignee: UNIVERSITY OF GEORGIA RESEARCH FOUNDATION, INC., Athens, GA (US)

(*) Notice: Subject to any disclaimer, the term of this patent is extended or adjusted under 35 U.S.C. 154(b) by 0 days.

(21) Appl. No.: 14/809,712

(22) Filed: Jul. 27, 2015

(65) Prior Publication Data

US 2016/0060638 A1    Mar. 3, 2016

Related U.S. Application Data

(60) Provisional application No. 62/044,667, filed on Sep. 2, 2014.

(51) Int. Cl.
| | |
|---|---|
| *C12P 13/04* | (2006.01) |
| *C12P 13/22* | (2006.01) |
| *C12N 9/02* | (2006.01) |
| *C12N 9/88* | (2006.01) |
| *C12N 9/10* | (2006.01) |
| *C12N 9/12* | (2006.01) |
| *C12N 1/21* | (2006.01) |

(52) U.S. Cl.
CPC ......... *C12N 9/0073* (2013.01); *C12N 9/0071* (2013.01); *C12N 9/1022* (2013.01); *C12N 9/1077* (2013.01); *C12N 9/1085* (2013.01); *C12N 9/1205* (2013.01); *C12N 9/1294* (2013.01); *C12N 9/88* (2013.01); *C12P 13/04* (2013.01); *C12P 13/227* (2013.01); *C12Y 114/13* (2013.01)

(58) Field of Classification Search
None
See application file for complete search history.

(56) References Cited

U.S. PATENT DOCUMENTS 5,756,345 A    5/1998    Camakaris et al.

FOREIGN PATENT DOCUMENTS

| WO | WO 95/34657 A2 | 12/1995 |
| WO | WO2012135389 A2 * | 10/2012 |
| WO | WO 2015/175793 A1 | 11/2015 |

OTHER PUBLICATIONS

Smith et al., 5-hdyroxanthranilic acid, a tryptophan metabolite, generates oxidative stress and neuronal death via p38 activation in cultured cerebellar granule neurons, Neurotox Res., 2009, 15, 303-10.*

Sun et al., Precursor-directed biosynthesis of 5-hydroxytryptophan using metabolically engineered *E. coli*, ACS Synthetic Biol., Oct. 2014, 4, 554-558.*

Ajikumar et al., "Isoprenoid pathway optimization for Taxol precursor overproduction in *Escherichia coli*" *Science*, 2010; 330:70-74.

Atsumi et al. "Non-fermentative pathways for synthesis of branched-chain higher alcohols as biofuels" *Nature*, Jan. 3, 2008; 451(7174):86-9.

Balderas-Hernandez et al., "Metabolic engineering for improving anthranilate synthesis from glucose in *Escherichia coli*" *Microb. Cell Fact.* 2009; 8:19.

BiotecEra, "BiotecEra Recived NSF STTR Award" News release, Jun. 22, 2015; [available online] Retrieved Nov. 14, 2016 <http://www.biotecera.com/single-post/2015/06/22/BiotecEra-receives-NSF-STTR-Award> 2 pages.

Birdsall, "5-Hydroxytryptophan: a clinically-effective serotonin precursor" *Altern. Med. Rev.* Aug. 1998; 3(4):271-80.

Frangatos and Chubb, "A new synthesis of 5-hydroxytryptophan" *Can J Chem*, 1959; 37:1374-6.

Gerhardt et al. (eds.) *Methods for General and Molecular Bacteriology*, American Society for Microbiology, 1994; Cover page, publisher's page, and chapters 13-14 and 16-18.

Hamdan and Ribeiro, "Characterization of a stable form of tryptophan hydroxylase from the human parasite *Schistosoma mansoni*" *J. Biol. Chem.*, 1999; 274:21746-54.

Hickey et al., "Cloning, Nucleotide Sequencing, and Functional Analysis of a Novel, Mobile Cluster of Biodegradation Genes from Pseudomonas aeruginosa Strain JB2" Appl. Environ. Microbiol, 2001; 67(10):4603-9. Huang et al., "Caffeic acid production enhancement by engineering a phenylalanine over-producing *Escherichia coli* strain," Dec. 2013 *Biotechnol. Bioeng.* 110:3188-3196. Available online on Jul. 11, 2013.

Ishiyama et al., "Novel pathway of salicylate degradation by *Streptomyces* sp. strain WA46" *Appl. Environ. Microbiol.* 2004; 70(3):1297-306.

Lin et al, "Microbial Biosynthesis of the Anticoagulant Precursor 4-Hydroxycoumarin" Nature Communications, Oct. 16, 2013, 4:2603. 8 pages.

(Continued)

*Primary Examiner* — Robert Mondesi
*Assistant Examiner* — Todd M Epstein
(74) *Attorney, Agent, or Firm* — Mueting, Raasch & Gebhardt, P.A.

(57) ABSTRACT

The invention provides compounds, compositions, non-naturally occurring organisms, and methods useful for production of 5-hydroxytryptophan (5-HTP) in a microbial cell. A microbial system which includes at least one microbial cell, such as a bacterial cell or a yeast cell, is genetically engineered to express all or a portion of non-naturally occurring biosynthetic pathway that catalyzes the conversion of a simple carbon source, such as glucose, to 5-HTP. The invention can result in improved titers of 5-HTP and permits low-cost, large scale production. Methods of making and using the genetically engineered cells are also included in the invention.

28 Claims, 8 Drawing Sheets

(56) References Cited

OTHER PUBLICATIONS

Lin et al., "Combinatorial biosynthesis of plant-specific coumarins in bacteria" Metab. Eng., 2013; 18:69-77. Epub Apr. 30, 2013.
Lin et al. "Extending shikimate pathway for the production of muconic acid and its precursor salicylic acid in *Escherichia coli*" Metab. Eng., 2014; 23:62-69. Epub Feb. 25, 2014.
Lin et al., "Biotechnological production of plant-specific hydroxylated phenylpropanoids" Biotechnol Bioeng, 2014; 111(9):1895-9. Epub Apr. 18, 2014.
Lin et al., "Engineering bacterial phenylalanine 4-hydroxylase for microbial synthesis of human neurotransmitter precursor 5-hydroxytryptophan" ACS Synth Biol, Jul. 18, 2014; 3(7):497-505. Jun. 17, 2014.
Lin et al., "Engineering bacterial phenylalanine 4-hydroxylase for microbial synthesis of human neurotransmitter precursor 5-hydroxytryptophan" ACS Synth Biol, Jul. 18, 2014; 3(7):497-505 (Supporting Information). Jun. 17, 2014.
Lin et al., "Microbial Production of a Multi-Functional Drug 5-Hydroxytryptophan via Combined Metabolic and Protein Engineering Approaches" 2014 AIChE Annual Meeting, Nov. 16-21, 2014, Atlanta, GA, Abstract No. 386996, Nov. 20, 2014, [retrieved on Nov. 14, 2016], 1 pg. Retrieved from the Internet: <URL:aiche.confex.com/aiche/2014/webprogram/Paper386996>.
Sambrook et al., Molecular Cloning: A Laboratory Manual, 2nd edition, 1989; Spring Harbor Laboratory Press, Cold Spring Harbor, NY; face page, copyright page, and Table of Contents, 32 pages.

"STTR Phase I: Microbial Production of a Multifunctional Natural Product 5-Hydroxytryptophan" Grant Abstract, Grant No. 1520927 [online]. Granted by the National Science Foundation, project dates Jul. 1, 2015 to Dec. 31, 2016 (Estimated) to Y. Lin and Y. Yan [retrieved on Nov. 14, 2016]. Retrieved from the Internet:<URL: https://www.nsf.gov/awardsearch/showAward?AWD_ID=1520927&HistoricalAwards=false >; 2 pgs.
Sun et al., "A novel muconic acid biosynthesis approach by shunting tryptophan biosynthesis via anthranilate" Appl. Environ. Microbiol. 79, 4024-30. Epub Apr. 19, 2013.
Sun et al., "Precursor-directed biosynthesis of 5-hydroxytryptophan using metabolically engineered *E. coli*" ACS Synth Biol, 2015; 4(5):554-8. (Supporting Information) Epub Oct. 2, 2014.
Westfall et al., "Production of amorphadiene in yeast, and its conversion to dihydroartemisinic acid, precursor to the antimalarial agent artemisinin" *Proc. Natl. Acad. Sci. U. S. A.*, Jan. 17, 2012; 109(3):E111-118.
Xu et al. "Modular optimization of multi-gene pathways for fatty acids production in *E. coli*." *Nat. Commun.* 2013; 4:1409. Epub Jan. 29, 2013.
Zhang et al., "PqsD is responsible for the synthesis of 2,4-dihydroxyquinoline, an extracellular metabolite produced by *Pseudomonas aeruginosa*" *J. Biol. Chem.* 2008; 283(43):28788-94.
Zhang et al., "Expanding metabolism for biosynthesis of nonnatural alcohols" Proc. Natl. Acad. Sci. U.S.A., 2008; 105:20653-8.
Zhou et al., "Salicylate 5-Hydroxylase from *Ralstonia* sp. Strain U2: a Monooxygenase with Close Relationships to and Shared Electron Transport Proteins with Naphthalene Dioxygenase" J Bacteriol, 2002; 184(6):1547-55.

* cited by examiner

PRECURSOR-DIRECTED BIOSYNTHESIS OF 5-HYDROXYTRYPTOPHAN

This application claims the benefit of U.S. Provisional Application Ser. No. 62/044,667, filed Sep. 2, 2014, which is incorporated herein by reference in its entirety.

BACKGROUND

5-Hydroxytryptophan (5-HTP) is a natural non-proteinogenic amino acid that serves as a direct biosynthetic precursor to the neurotransmitter serotonin. Deficient serotonin in the central nervous system (CNS) is thought to be an important physiological factor for depression. 5-HTP has been shown to be effective for the treatment of a variety of conditions, including depression, insomnia, chronic headaches and binge eating associated with obesity. At the same time, it has relatively few side effects. The therapeutic efficacy of 5-HTP is due to its ability to enhance the synthesis of serotonin in the brain. 5-HTP is well absorbed from an oral dose and can easily cross the blood-brain barrier (Birdsall, 1998 Altern. Med. Rev. 3:271-280). In most European countries, 5-HTP is a commonly prescribed drug for multiple treatment purposes; while in North America market it is sold as an "over-the-counter" dietary supplement.

Currently, 5-HTP is obtained through extraction from the seeds of *Griffonia simplicifolia*, a woody climbing shrub grown in Africa. The season- and region-dependent supply of the raw materials has been largely limiting its cost-effective production and broad clinical applications. In addition, *Griffonia* derived 5-HTP has been contaminated with a compound called Peak X, leading to the USDA briefly removing the supplement from shelves in the US. The current bulk wholesale price for 5-HTP ranges from 400 to 1000 USD/kg. Yet despite the current high production cost and limited supply, the global market of 5-HTP is still about 50,000 kg (bulk value 20-50 million dollars).

SUMMARY OF THE INVENTION

The invention provides novel metabolically engineered microbial cells, as well as methods of using said cells for microbial production of 5-hydroxytryptophan (5-HTP) from a simple carbon source, such as glucose. More particularly, the invention provides a novel microbial system that includes one or more microbial cells that are genetically engineered to express all or a portion of a novel metabolic pathway for the production of 5-HTP. The novel metabolic pathway employs one or more enzymes having relaxed substrate selectivity, which are advantageously utilized within the novel metabolic pathway to catalyze reactions involving one or more non-natural substrates. The entire biosynthetic pathway may be incorporated into a single microbial cell; however, it was found that production of 5-HTP improved when two microbial cells were employed, a first cell incorporating the upstream portion of the pathway, producing a 5-hydroxyanthranilate (5-HAA) intermediate, and a second cell incorporating the downstream portion of the pathway, producing the 5-HTP end product. Methods of making and using the genetically engineered cells are also included in the invention, which include but are not limited to methods for making 5-HTP or any of its precursors, such as 5-HAA. Such methods can include culturing one or more genetically engineered cells described herein under conditions and for a time sufficient to produce 5-HTP or any of its precursors, and optionally isolating the product.

The method can further include incorporating the 5-HTP into a food product. The food product can be fit for human consumption and/or it can be an animal feed or a beverage. The method can include packaging the 5-HTP or food product for sale and optionally providing instructions for use of the 5-HTP or food product as a food additive, a food supplement, or a nutraceutical. In one embodiment, the food additive, food supplement, or nutraceutical is packaged for use as an animal feed or beverage.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Abbreviations

AA Anthranilate
5-HAA 5-Hydroxyanthranilate
5-HI 5-Hydroxyindole
TP or Trp Tryptophan
5-HTP 5-Hydroxytryptophan
SA Salicylate
GA Gentisate

TrpDCA and TrpB: *E. coli* native tryptophan biosynthetic enzymes. In a two cell system, *E. coli* BW3 is an exemplary strain that incorporates the upstream portion of the biosynthetic pathway, yielding 5-hydroxyanthranilate (5-HAA); *E. coli* BW2 is an exemplary strain that incorporates the downstream portion of the biosynthetic pathway.

Figure 1A:
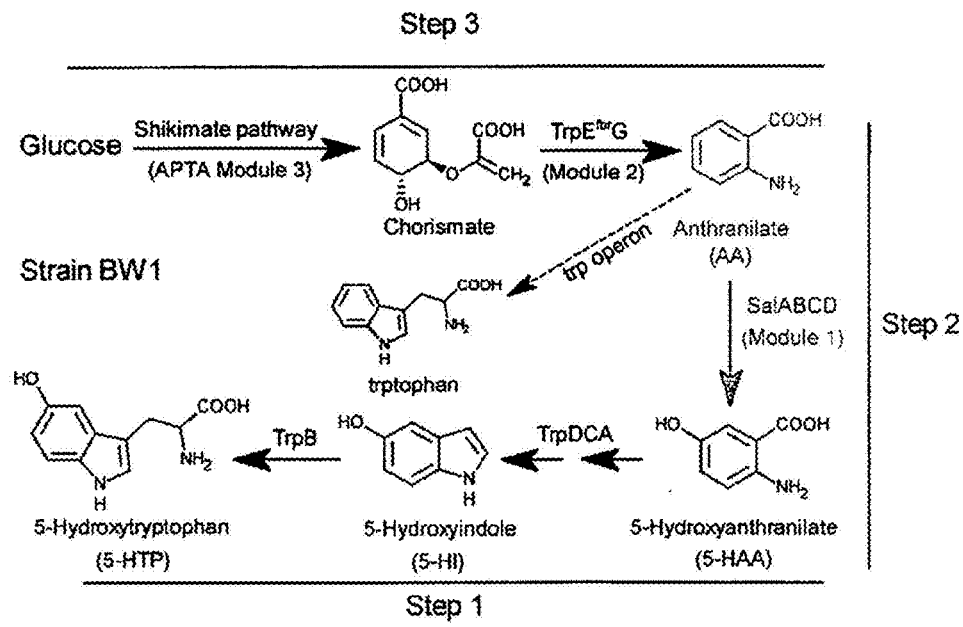
FIG. 1A shows an example of a novel 5-HTP biosynthetic pathway. TrpE$^{fbr}$G: anthranilate synthase (feedback resistance mutant); SalABCD: salicylate 5-hydroxylase; TrpDCA and TrpB: *Escherichia coli* native tryptophan biosynthetic enzymes. The dotted line shows possible shunting of carbon toward tryptophan via the action of tryptophan biosynthetic enzymes. *E. coli* BW1 is an exemplary strain that incorporates the full biosynthetic pathway.
Figure 1B:
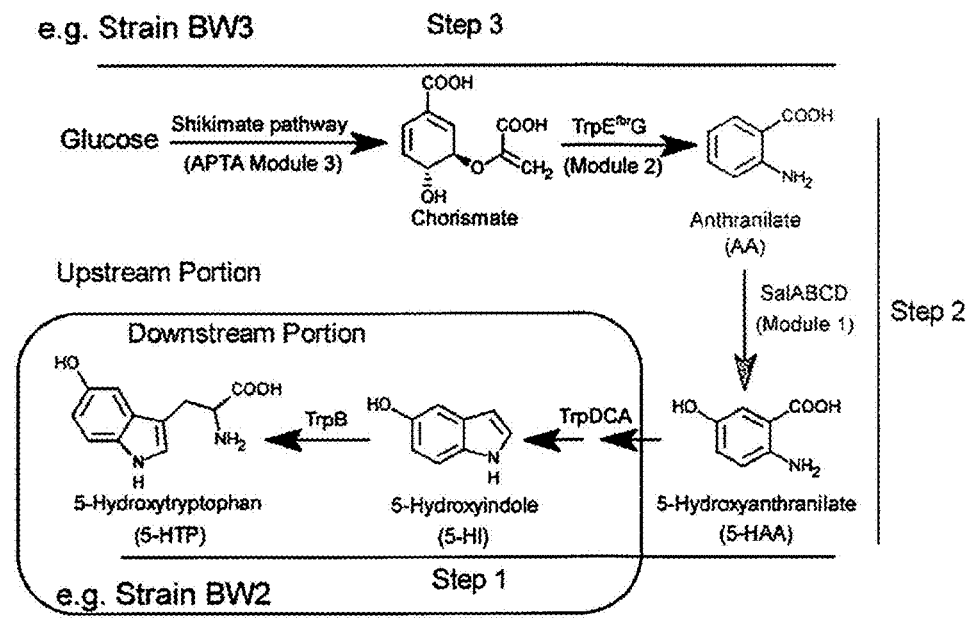
FIG. 1B shows another example of a novel 5-HTP biosynthetic pathway, divided into an upstream and downstream portion. TrpE$^{fbr}$G: anthranilate synthase (feedback resistance mutant); SalABCD: salicylate 5-hydroxylase.

Steps 1, 2 and 3 shown in FIGS. 1A and 1B represent the steps used to reverse engineer the microbial synthesis of 5-HTP as described in Example 1, with step 1 representing the most downstream step and step 3 representing the most upstream step.

Figure 1C:
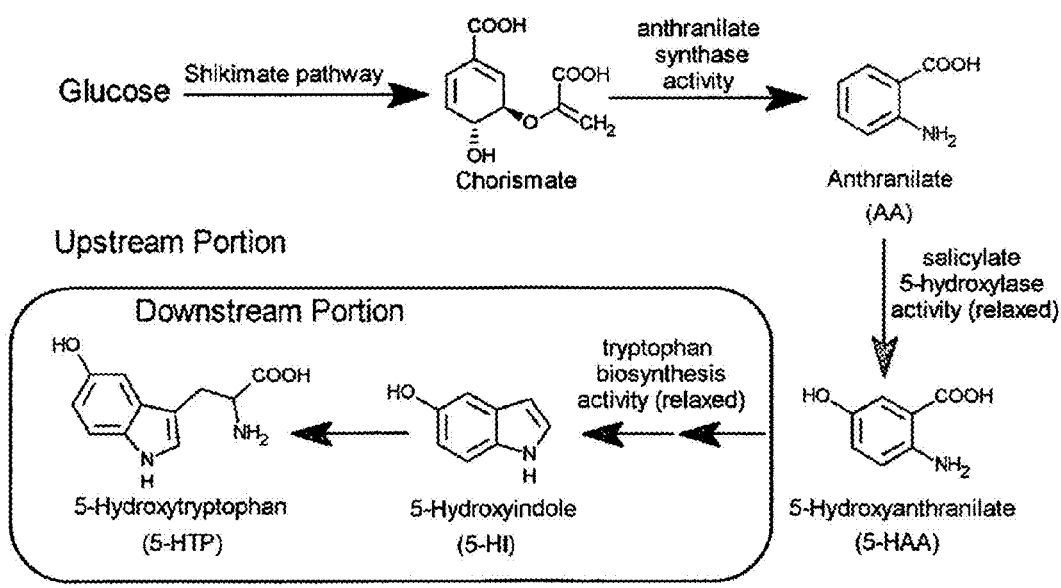

FIG. 1C shows a further example of a novel 5-HTP biosynthetic pathway, divided into an upstream and downstream portion, which pathway employs salicylate 5-hydroxylase and tryptophan biosynthesis activities that exhibit relaxed substrate selectivity.

Figure 2A:
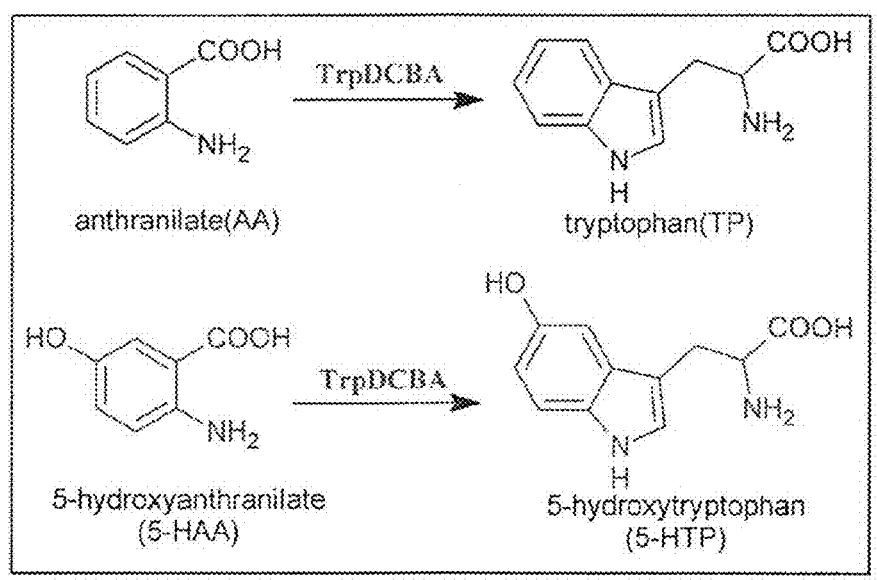

FIG. 2A shows the conversion of anthranilate (AA) to tryptophan (TP), catalyzed by TrpDCBA (top panel) and the the analogous conversion of 5-hydroxyanthranilate (5-HAA) to 5-hydroxytryptophan (5-HTP), also catalyzed by TrpDCBA (bottom panel).

Figure 2B:
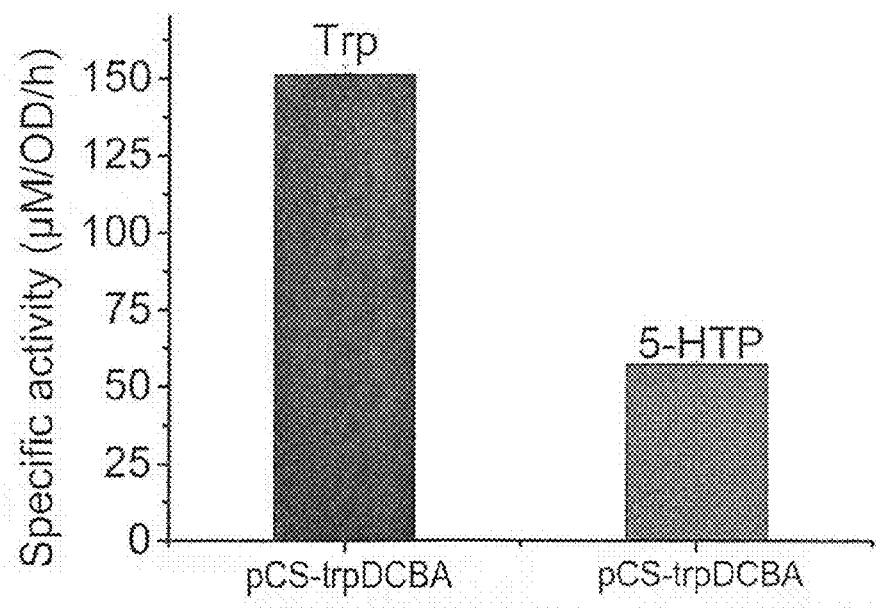

FIG. 2B shows in vivo assays of TrpDCBA towards the natural substrate AA (black) and the non-natural substrate 5-HAA (grey). Strain BW2 harboring plasmid pCS-trpDCBA was used for the in vivo assays. The product of each reaction was shown on the top of each bar. Trp: tryptophan.

Figure 3A:
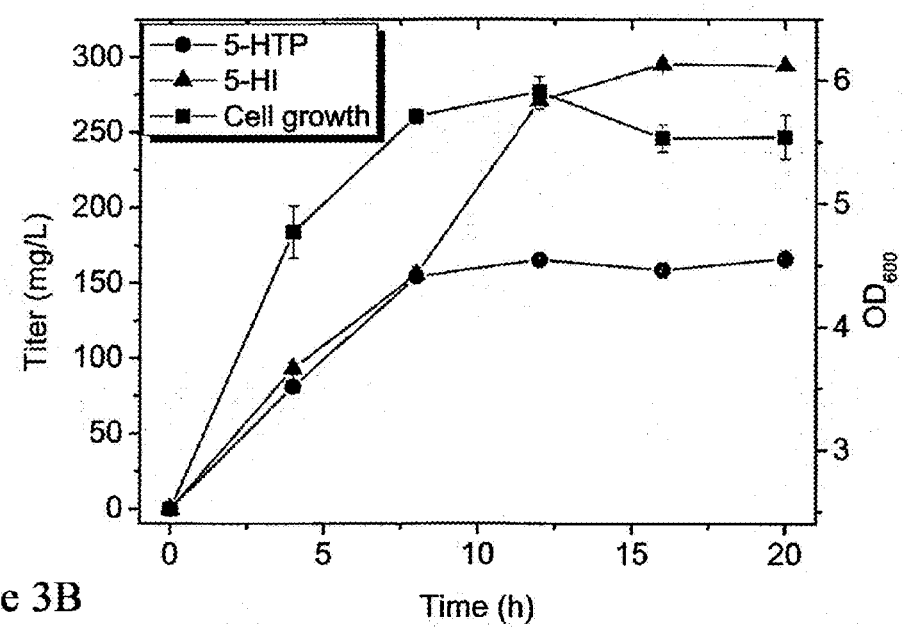

FIG. 3A shows bioconversion of 5-HAA to 5-HTP using strain BW2 harboring low-copy-number plasmid pSA-trpDCBA. 5-HAA (600 mg/L) was fed to the cultures at 0 h and 10 h. Samples were taken every four hours and analyzed by HPLC.

Figure 3B:
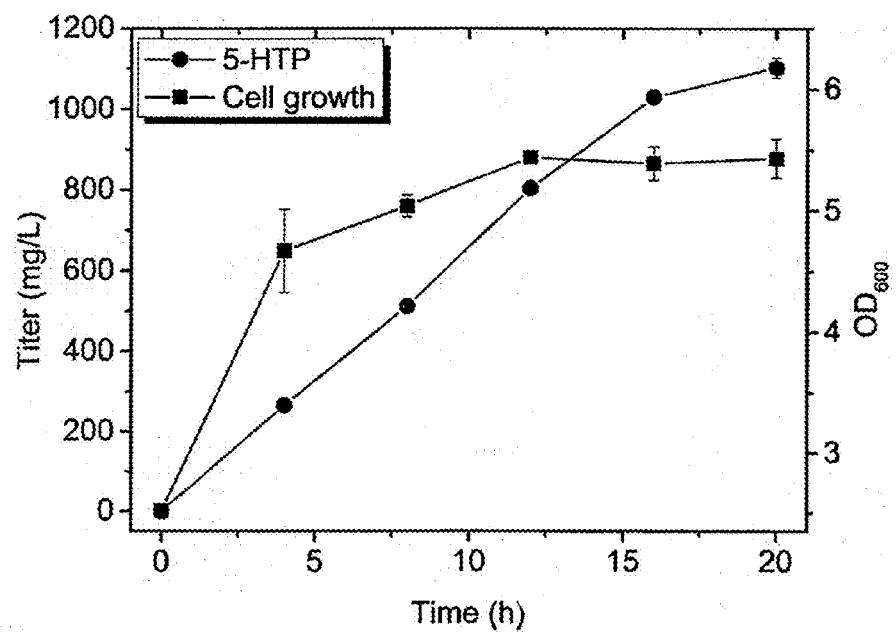

FIG. 3B shows bioconversion of 5-HAA to 5-HTP using strain BW2 harboring medium-copy-number plasmid pCS-trpDCBA. 5-HAA (600 mg/L) was fed to the cultures at 0 h and 10 h. Samples were taken every four hours and analyzed by HPLC.

Figure 4A:
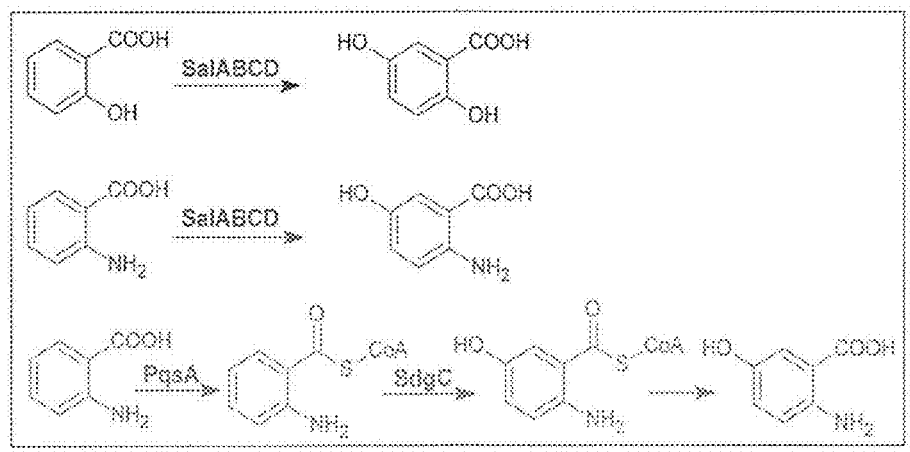

FIG. 4A shows the native bacterial conversion of salicylate into gentisate (GA) catalyzed by SalABCD (top panel); the conversion of AA into 5-HAA catalyzed by SalABCD, as salicylate (2-hydroxybenzoate) and AA (2-aminobenzoate) have similar molecular structures (middle panel); and the conversion of AA into 5-HAA catalyzed by sequential action of an anthraniloyl-CoA synthetase (PqsA) and a salicyloyl-CoA 5-hydroxylase (SdgC) (bottom panel).

Figure 4B:
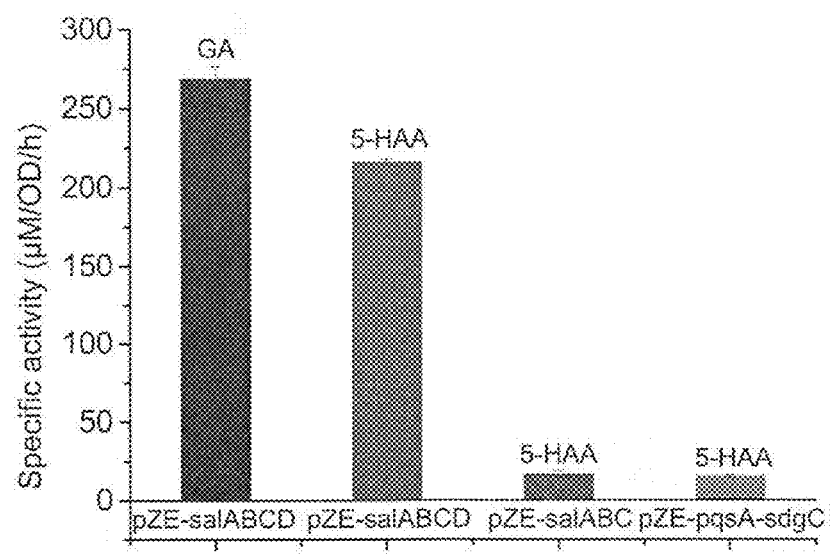

FIG. 4B shows in vivo assays of anthranilate 5-hydroxylases. Strain BW3 was used as the host. Plasmids used were shown below each bar. The product of each reaction was shown on the top of each bar.

Figure 5:
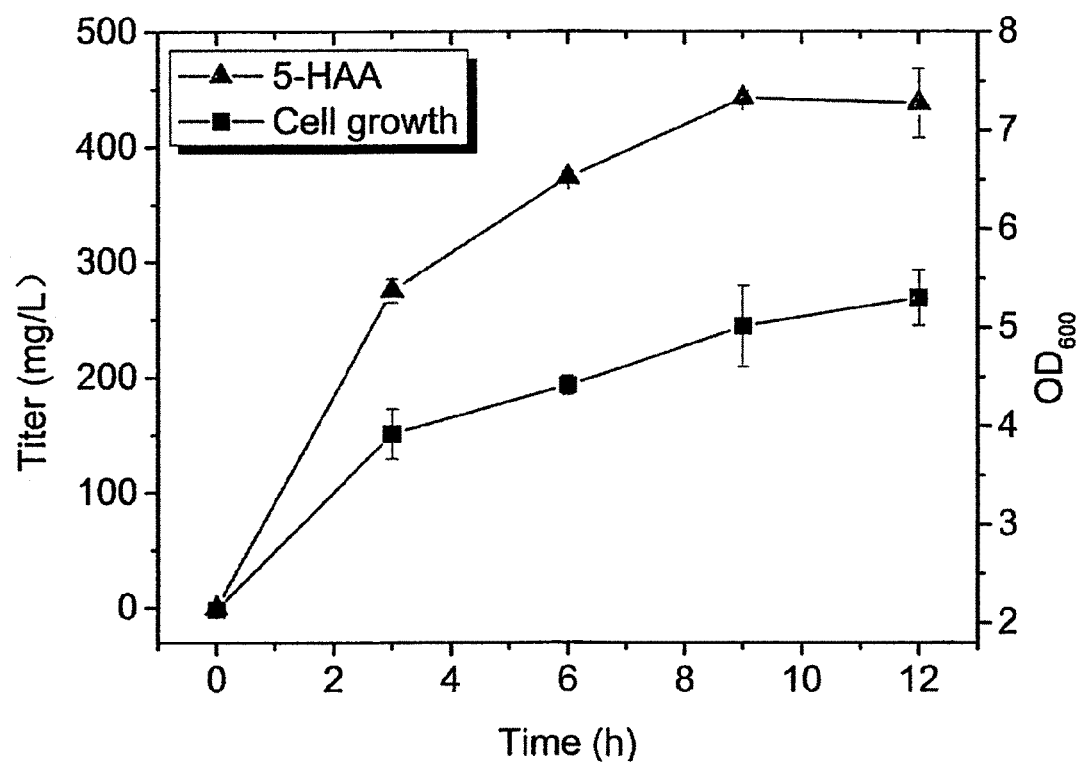

FIG. 5 shows bioconversion of AA to 5-HAA. Strain BW3 harboring pZE-salABCD was used for the bioconversion. 5-HAA (300 mg/L) was fed to the culture at 0 h and 5 h. Samples were taken every three hours and analyzed by HPLC.

Figure 6:
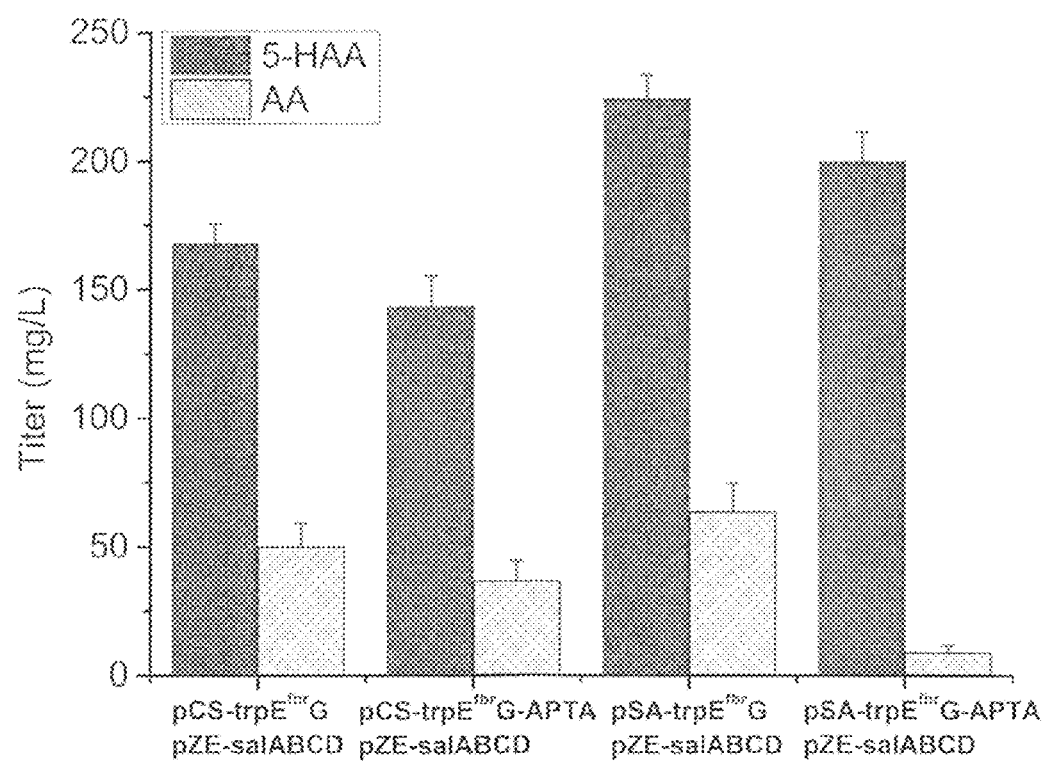

FIG. 6 shows modular optimization of 5-HAA production from glucose. Strain BW3 was used as the host. Plasmids used were shown below each bar.

Figure 7A:
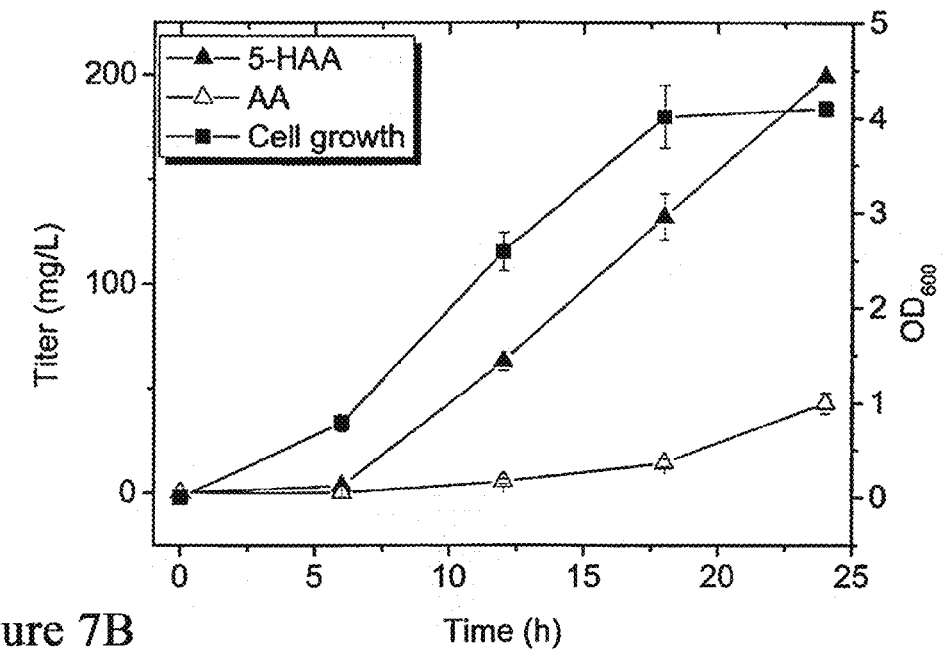

FIG. 7A shows 5-HAA production from glucose using strain BW3 harboring plasmids pZE-salABCD and pSA-trpE$^{fbr}$G, the first part (upstream portion) of a two-step strategy for 5-HTP production.

Figure 7B:
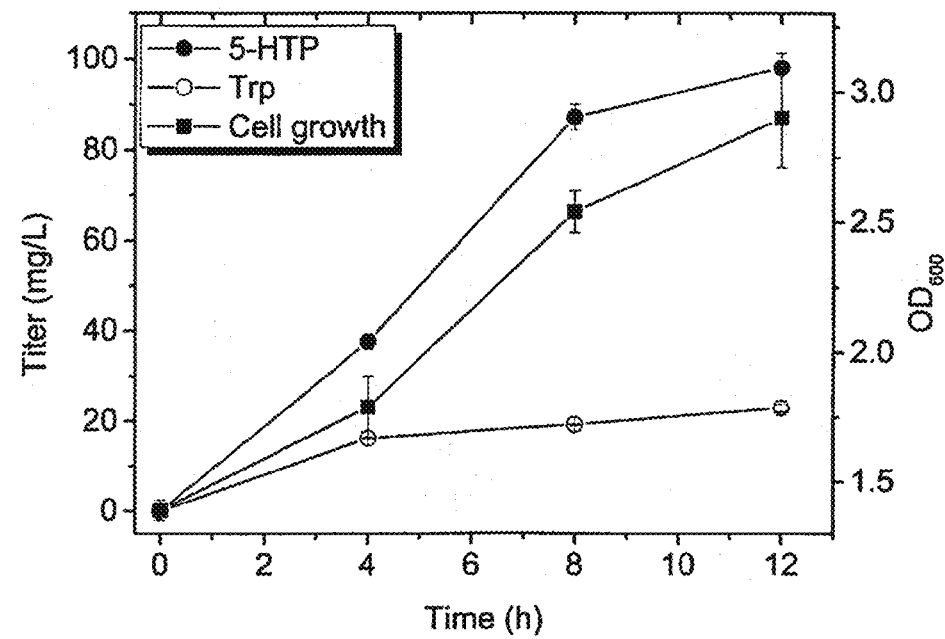

FIG. 7B shows 5-HTP production from 5-HAA using strain BW2 harboring plasmids harboring pCA-trpDCBA and pSA-trpDCBA, the second part (downstream portion) of a two-step strategy for 5-HTP production.

DETAILED DESCRIPTION OF ILLUSTRATIVE EMBODIMENTS

The invention provides a novel biosynthetic pathway leading to the production of 5-hydroxytryptophan (5-HTP) from glucose, via a 5-hydroxyanthranilate (5-HAA) precursor. Until now, the only reported 5-HTP biosynthetic pathway is via tryptophan, and the reaction is catalyzed by tryptophan 5-hydroxylase (T5H). However, T5H is unstable when expressed in microorganisms and requires a special co-factor 5,6,7,8-tetrahydrobiopterin (BH4) that should be regenerated by additional enzyme reactions (Hamdan and Ribeiro, 1999 J. Biol. Chem. 274:21746-21754; Lin et al., 2014, *ACS Synth. Biol.* 3(7):497-505). These problems hamper the application of this pathway to the economical production of 5-HTP. To circumvent problems associate with 5-HTP production, we reverse engineered a novel biosynthetic pathway for 5-HTP production by identifying and employing selected pathway enzymes that exhibit substrate tolerance, thus implementing the concept of precursor-directed biosynthesis (FIG. 1). By taking advantage of the relaxed substrate selectivities of these enzymes, we circumvented the need to rely on the unstable tryptophan 5-hydroxylase.

The first step in reverse engineering the novel biosynthetic pathway, corresponding to the downstream part of the metabolic pathway, was to find a simple precursor to 5-HTP. 5-Hydroxyanthranilate (5-HAA) was identified as a suitable precursor. In the *E. coli* tryptophan biosynthetic pathway, the precursor anthranilate (AA) is converted into tryptophan (TP) via enzymatic reactions catalyzed by TrpDCBA (FIG. 2A, top panel). Using in vivo assays we were surprised to discover that 5-hydroxyanthranilate (5-HAA) can be converted into 5-HTP via enzymatic reactions that are also catalyzed by TrpDCBA (FIG. 2B, bottom panel). Thus, 5-HAA was identified as a simple precursor to 5-HTP.

In the upstream portion of the novel biosynthetic pathway, a novel salicylate 5-hydroxylase (S5H) is used to convert the non-natural substrate anthranilate (AA) to the precursor 5-HAA. Production of 5-HAA from glucose is optionally further enhanced using modular optimization of modules involved in production of upstream intermediates chorismate and anthranilate as well as 5-HAA (FIG. 1), as described in more detail below.

In the downstream portion of the novel biosynthetic pathway, 5-HTP is produced from a 5-hydroxyanthranilate (5-HAA) precursor by the catalysis of *E. coli* TrpDCBA.

The enzymes expressed in the cells of the invention may be heterologous with respect to the host cells, or they may be naturally found in the host cell organism. For example, when *E. coli* is a host organism, one or more on the enzymes that are employed in the biosynthetic pathway can be native *E. coli* enzymes, and one or more of the expressed enzymes can be from other (non-*E. coli*) organisms (i.e., heterologous). When an enzyme that is native to the host organism is expressed from a plasmid or other vector, that enzyme is overexpressed in the host organism relative to a host organism without plasmid. Overexpression of naturally occurring enzymes, and expression of enzymes from other hosts, via multiple plasmids or other vectors, allows optimization and fine-tuning of the various enzymes that make up the overall genetically engineered biosynthetic pathway.

Although the full pathway can be incorporated into a single cell, the invention preferably utilizes a two-stage strategy, also referred to herein as a two-step strategy, wherein the upstream and downstream portions of the biosynthetic pathway are incorporated into two different cells, in order to optimally achieve the de novo production of 5-HTP. More generally, the inventive strategy and concept is applicable design and establishment of non-natural pathways for the biosynthesis of other chemicals.

The present invention thus includes microbial cells that are genetically engineered to produce 5-HTP or an intermediate in the biosynthetic pathway leading up to 5-HTP, as well methods for making said cells and methods for producing and isolating 5-HTP from said cells or cell culture. The invention involves genetically engineering a microbial cell to express all or a portion of a novel biosynthetic pathway for the microbial biosynthesis of 5-HTP from simple carbon sources. The present invention provides a cost-effective microbial process for the efficient production of 5-HTP from inexpensive carbon sources. This technology is expected to facilitate creation of a biocatalytic platform to convert cheap feedstock to the high purity product 5-HTP, which will dramatically lower its production cost compared with the conventional extraction approach, greatly improve its availability to the less well-treated patients, and further expand its market.

Examples of microbial cells that can be engineered to express the 5-HTP biosynthesis pathway as well as methods for making said cells and methods for producing and isolating 5-HTP are described in more detail below.

Upstream Biosynthetic Pathway

5-Hydroxylation of anthranilate (AA) to yield 5-hydroxyanthranilate (5-HAA). As noted above, 5-hydroxyanthranilate (5-HAA) was identified as the target precursor for the biosynthesis of 5-HTP. The next step in reverse engineering the novel biosynthetic pathway (upstream of the first step) was to find a way to synthesize 5-HAA from a primary metabolite. Anthranilate (AA) was identified as a primary metabolite. AA is a potential precursor of 5-HAA because 5-hydroxylation of AA will lead to the formation of 5-HAA. However, no AA 5-hydroxylases have been reported.

Surprisingly, it was found that a salicylate 5-hydroxylase (S5H), which natively catalyzes the hydroxylation of salicylate (SA) to yield gentisate (GA), exhibits relaxed substrate selectivity and is able to also catalyze the hydroxylation of the non-natural substrate AA to yield 5-HAA. The term "relaxed substrate selectivity" means that the enzyme can catalyze a a reaction, in this case 5-hydroxylation, of a non-native substrate. To our knowledge, this is the first report of a salicylate 5-hydroxylase (S5H) that is able to use AA as a substrate. The discovery of a novel S5H having relaxed substrate selectivity and the ability to convert AA to 5-HAA is notable because the S5H can be expressed in a metabolically engineered microorganism of the invention to increase 5-HAA synthesis.

A preferred S5H for use in the novel biosynthetic pathway of the invention is an S5H from *Ralstonia eutropha* H16 designated as SalABCD; however, the invention is not limited to a particular S5H. In some embodiments, the S5H includes at least one of SalA, SalB, SalC, and SalD. Preferably, the S5H includes SalA, SalB, SalC, and SalD. In *R. eutropha* H16, SalA, SalB, SalC, and SalD are encoded by salA, salB, salC, and salD, respectively, which are present in a gene cluster. Thus, in embodiments where the S5H includes SalA, SalB, SalC, and SalD, they may be expressed by a single gene (salABCD) or by multiple genes (salAB and salCD) and may be referred to as SalABCD.

An enzyme having S5H activity may be obtained from any suitable organism. Other examples of suitable S5H enzymes include S5H from *Ralstonia* sp. strain U2 and *Pseudomonas aeruginosa* strain JB2 (Zhou et al., 2002 J. Bacteriol. 184:1547-1555; Hickey et al., 2001 Appl. Environ. Microbiol. 67:4603-4609). Preferably, the S5H enzyme is a *R. eutropha* H16S5H enzyme. Preferably, the *R. eutropha* H16S5H enzyme is encoded by salABCD and is present in a high-copy-number plasmid.

In some embodiments, S5H activity may include two or more enzymes used in combination. For example, an anthraniloyl-CoA synthetase (encoded by pqsA) and a salicyloyl-CoA 5-hydroxylase (encoded by sdgC) may be used in a sequential catalyzation to convert AA into 5-HAA. Where the S5H activity includes sequential reaction of an anthraniloyl-CoA synthetase and a salicyloyl-CoA 5-hydroxylase, the pqsA may be an *Pseudomonas aeruginosa* gene and the sdgC may be a *Streptomyces* sp. gene.

The novel biosynthetic pathway of the instant invention thus includes one or more enzymes having a relaxed salicylate 5-hydroxylase activity (S5H) that is capable of catalyzing the 5-hydroxylation of AA. The term "salicylate 5-hydroxylase" means any molecule or molecules having S5H activity; i.e., that is able to catalyze the conversion of SA to GA; and a suitable S5H is one that has relaxed selectivity such that it is also able to 5-hydroxylate AA to yield 5-HAA. The term S5H includes any naturally occurring S5H as well as any fragment or modification thereof, including enzymes encoded by insertion, deletion, or mutation of a naturally occurring S5H, provided S5H activity is retained. The S5H may be endogenous to the cell, or heterologous to the cell. The gene encoding the S5H can be genomically integrated into the host cell or expressed from one or more extrachromosomal elements, such as a plasmid.

Enzymatic Synthesis of Anthranilate (AA).

The upstream pathway for production of 5-HAA also includes enzymes involved in the multi-step conversion of glucose to chorismate, for example one or more enzymes in the shikimate pathway, as well as one or more enzymes that catalyze the subsequent conversion of chorismate to AA, i.e., that have anthranilate synthase activity (see FIG. 1). The novel biosynthetic pathway of the instant invention thus further includes one or more enzymes involved in chorismate synthesis, such as shikimate pathway enzymes, and one or more enzymes having anthranilate synthase activity.

The shikimate pathway involved multiple enzymes and constitutes a metabolic route used by bacteria, fungi, algae, parasites and plants for the biosynthesis of aromatic amino acids. Chorismate is an intermediate metabolite in this pathway. It should be understood that while the most upstream segment of the overall engineered metabolic pathway of the invention is generally referred to herein as the shikimate pathway (see FIG. 1), since shikimate is an upstream metabolite of chorismate, the term shikimate pathway enzymes is to be understood to broadly encompass enzymes involved in the biosynthesis of chorismate.

The shikimate pathway can include a shikimate kinase, a phosphoenolpyruvate synthase, a transketolase, and a 3-deoxy-D-arabinoheptulosonate 7-phosphate (DAHP) synthase. The enzymes involved in the production of the primary metabolite anthraniliate (AA) in *E. coli* are described in Sun et al. (2013 Appl. Environ. Microbiol. 79:4024-4030).

The genes encoding an enzyme involved in chorismate biosynthesis, such as a shikimate kinase, a phosphoenolpyruvate synthase, a transketolase, and/or a DAHP synthase, can be endogenous to the host cell, or they may be obtained from any suitable organism. The enzymes may be present in native amounts, or their expression can be enhanced by expressing additional copies of one or more of the endogenous gene(s) on one or more vectors, such as a plasmid, introduced into the host cell. In other embodiments, one or more of the genes encoding a shikimate kinase, a phosphoenolpyruvate synthase, a transketolase, and a DAHP synthase may be obtained from different organisms and either genomically integrated into the host cell or expressed from one or more or extrachromosomal elements, such as a plasmid. It should be understood that in host organisms that possess an endogenous pathway for the synthesis of chorismate, such that the cell is able to produce the metabolite chorismate, the inclusion of an extrachromosomal element such as a plasmid that operably encodes one or more shikimate pathway enzymes (such as the "APTA" module described below and in Example I), whether endogenous to the cell or heterologous to the cell, is optional.

In some embodiments a shikimate kinase is encoded by aroL, a phosphoenolpyruvate synthase is encoded by ppsA, a transketolase is encoded by tktA, and a DAHP synthase is encoded by aroG. One or more of the enzymes in the shikimate pathway may be a feedback inhibition mutant. A "feedback inhibition mutant" does not respond to cellular control mechanisms intended to limit enzymatic activity and will continue to catalyze a reaction even after the product has accumulated to physiological useful levels. For example, aroG encodes a feedback inhibition mutant DAHP synthase. The shikimate pathway may be obtained from any suitable organism. For example, a shikimate pathway may be an $E.\ coli$ shikimate pathway. In a preferred embodiment, a novel biosynthetic pathway includes an $E.\ coli$ shikimate pathway which includes an APTA module including a shikimate kinase (aaroL), a phosphoenolpyruvate synthase (ppsA), a transketolase (ttktA), and a DAHP synthase (aroG) which is a feedback inhibition mutant (encoded by aroG$^{fbr}$). This module is associated with enhanced chorismate availability. The APTA module expresses one or more enzymes that increase carbon flow toward chorismate. Exemplary components of the first module are described, for example, in Lin et al., 2013 Nat. Commun. 4:2603.

An enzyme having anthranilate synthase activity includes, in one embodiment, at least one of TrpE or TrpG from the tryptophan biosynthesis pathway. In a preferred embodiment, the anthranilate synthase activity can be supplied by a combination of TrPE and TrpG. In $E.\ coli$, TrpE and TrpG are encoded by trpE and trpG, respectively, which are present in a gene cluster. Thus, in embodiments where anthranilate synthase activity is provided by expression in the host cell of both TrpE and TrpG, they may be expressed by a single gene (trpEG) and may be referred to as TrpEG. The anthranilate synthase may also include a feedback inhibition mutant. For example, trpE$^{fbr}$G encodes a feedback inhibition mutant anthranilate synthase. Preferably, when the host cell expresses only the upstream portion of the biosynthetic pathway, the host cell is modified to delete natively occurring trpD.

The enzyme having anthranilate synthase activity may be endogenous to the host cell, or it may obtained from any suitable organism. $E.\ coli$ anthranilate synthase is an exemplary enzyme having anthranilate synthase activity. In one embodiment, a novel biosynthetic pathway includes an $E.\ coli$ TrpEG which is a feedback inhibition mutant (encoded by trpE$^{fbr}$G). Preferably, the $E.\ coli$ anthranilate synthase trpE$^{fbr}$G is present in a low-copy-number plasmid.

The enzyme having anthranilate synthase activity may be present in native amounts, or its expression can be enhanced by expressing additional copies of the endogenous gene(s) on a vector such as a plasmid introduced into the host cell. In other embodiments, a gene or genes encoding an anthranilate synthase activity may be obtained from a different organism and either genomically integrated into the host cell or expressed from one or more or extrachromosomal elements, such as a plasmid.

The enzyme having anthranilate synthase activity is not limited to any specific anthranilate synthase. The term "anthranilate synthase" means any molecule or molecules having anthranilate synthase activity; i.e., that is able to catalyze the conversion of chorismate to yield AA. The term anthranilate synthase includes any naturally occurring anthraniliate synthase as well as any fragment or any modification thereof, including enzymes encoded by insertion, deletion, or mutation of a naturally occurring anthranilate synthase, provided the anthranilate synthase activity is retained. The anthranilate synthase may be endogenous to the cell, or heterologous to the cell.

Pathway Optimization.

The upstream pathway (yielding 5-HAA) of the present invention can optionally be optimized by dividing it into three modules, then evaluating the effects of different copy numbers (i.e., expression levels) for the plasmids encoding the enzymes in each of the three modules. An exemplary optimization for an $E.\ coli$ host cell is described in Example I, and this example be readily generalized to other host cells. The modules were numbered moving progressively toward the most upstream segment. Module 1 consisted of salABCD, expressing S5H, which catalyzes the formation of 5-HAA from AA; module 2 was the trpE$^{fbr}$G module, expresses an enzyme with anthranilate synthase activity which catalyzes the conversion of chorismate to AA; and module 3 was the APTA module, which expresses four enzymes (AroL, PpsA, TktA, AroG$^{fbr}$) in the shikimate pathway to boost the carbon flux towards chorismate synthesis (Sun et al., 2013 Appl. Environ. Microbiol. 79:4024-4030). From the optimization results, a preferred embodiment of the upstream pathway is a host cell that includes a high copy number plasmid expressing S5H, such as pZE-salABCD as described in Example I, for module 1, and a low copy number plasmid expressing anthranilate synthase, such as pSA-trpEfbrG as described in Example I, for module 2. Expression of additional copies of the shikimate pathway enzymes in module 3 is optional provided the host cell natively expresses shikimate pathway enzymes so as to yield a chorismate metabolite, which is the metabolic precursor to AA. It should be understood more generally that in some embodiments, none of the enzymes in modules 1, 2 or 3 are expressed from a plasmid if the enzymes are present endogenously in a host cell; that is, overexpression via a plasmid or other vector of any endogenous enzymes is optional. It should be further understood that the invention is not limited to the particular enzymes exemplified in modules 1, 2 or 3; rather, any enzyme or set of enzymes that have the described activities, whether endogenous or heterologous, can be used in the metabolic pathway of the invention.

Downstream Biosynthetic Pathway

Synthesis of 5-HTP from 5-HAA. In the $E.\ coli$ tryptophan biosynthetic pathway, anthranilate (AA) is converted into tryptophan (TP) via enzymatic reactions that are catalyzed by TrpDCBA (FIG. 2A, top panel). Surprisingly, we discovered that TrpDCBA exhibits relaxed substrate selectivity, and that the non-native substrate 5-hydroxyanthranilate (5-HAA) can also be converted into 5-HTP via enzymatic reactions catalyzed by TrpDCBA (FIG. 2B, bottom panel).

The novel biosynthetic pathway of the instant invention thus includes one or more enzymes having tryptophan biosynthesis activity, and that exhibit relaxed substrate selectivity such that they can utilize 5-HAA as a substrate. The term "tryptophan biosynthesis activity" means, in this regard, the ability to catalyze the conversion of AA to tryptophan (TP) and is not limited to any specific tryptophan biosynthetic enzyme(s). Any enzyme(s) having tryptophan biosynthesis activity and that exhibits the ability to catalyze the conversion of 5-HAA to yield 5-HTP can be utilized. Enzymes with tryptophan biosynthesis activity include any naturally occurring tryptophan biosynthesis enzyme as well as any fragment or any modification thereof, including enzymes encoded by insertion, deletion, or mutation of a naturally occurring tryptophan biosynthesis enzyme, provided the tryptophan biosynthesis activity is retained. The tryptophan biosynthesis activity may be endogenous to the cell, or heterologous to the cell.

In some embodiments, the tryptophan biosynthesis activity is provided by at least one of TrpA, TrpB, TrpC, and TrpD. Preferably, the tryptophan biosynthesis activity is provided by TrpA, TrpB, TrpC, and TrpD. In *E. coli*, TrpA, TrpB, TrpC, and TrpD are encoded by trpA, trpB, trpC, and trpD, respectively, which are present in a gene cluster. In embodiments where the tryptophan biosynthesis activity is provided by TrpA, TrpB, TrpC, and TrpD, they may be expressed by a single gene (trpDCBA) or by multiple genes (e.g., trpA and trpDCB) and may be referred to as TrpD-CBA. For example, tryptophan biosynthesis activity may be an *E. coli* tryptophan biosynthesis activity. In one embodiment, a novel biosynthetic pathway includes an *E. coli* tryptophan biosynthesis pathway (encoded by trpDCBA). *E. coli* trpDCBA can be present on an vector, such as a plasmid. In some embodiments, the plasmid is a low-copy-number plasmid.

The tryptophan biosynthesis activity may be present in native amounts, or its expression can be enhanced by expressing additional copies of the endogenous gene(s) encoding the activity on vector such as a plasmid introduced into the host cell. In other embodiments, a gene or genes encoding a tryptophan biosynthesis activity may be obtained from a different organism and either genomically integrated into the host cell or expressed from one or more or extrachromosomal elements, such as a plasmid.

To summarize, the novel biosynthetic pathway catalyzes the conversion of a simple carbon source, such as glucose, to 5-HTP. The novel biosynthetic pathway includes 1) an upstream portion that catalyzes the conversion of the simple carbon source to 5-HAA, which upstream portion includes one or more shikimate pathway enzymes (i.e., enzymes involved in the production of chorismate), at least one enzyme having anthranilate synthase activity, and at least one enzyme having salicylate 5-hydroxylase (S5H) activity; and 2) a downstream portion that catalyzes the conversion of 5-HAA to 5-HTP via a tryptophan biosynthesis pathway. Both the upstream and downstream portions optionally, and preferably, include enzymes with relaxed substrate specificity that are recruited to utilize a non-native substrate in order to achieve production of a pathway intermediate or final product. Pathway enzymes can, independently, be endogenous to the host cell, or heterologous to the host cell. Endogenous enzyme activity can be supplied by the host cell without enhancement, or activity level can be augmented by additionally expressing the endogenous enzyme from an extrachromosomal element introduced into the host cell. In an exemplary embodiment, the novel biosynthetic pathway includes 1) an upstream portion that includes enzymes from an *E. coli* shikimate pathway, an *E. coli* trpE$^{fbr}$G anthranilate synthase, and a *R. eutropha* SalABCD salicylate 5-hydroxylase; and 2) a downstream portion that includes an *E. coli* tryptophan biosynthesis pathway (TrpDCBA).

Optionally, and advantageously, the upstream and downstream portions of the novel biosynthetic pathway may be engineered into two separate cells. More specifically, upstream and downstream portions of the novel biosynthetic pathway can be independently genetically engineered into in a first and a second microbial cell, respectively, thereby forming a microbial system that includes the first and second cells.

Host Cell

The present invention also provides a genetically engineered microbial cell capable of synthesizing 5-HTP by means of the novel biosynthetic pathway discussed herein. Specifically, the present invention provides microbial cells that are genetically engineered to express enzymes that catalyze the conversion of anthranilate (AA) to 5-hydroxyanthranilate (5-HAA) via 5-hydroxylation of anthranilate, and that catalyze the conversion of 5-HAA to 5-HTP. Optionally, the conversion of AA to 5-HAA (i.e., the upstream pathway) and the conversion of 5-HAA to 5-HTP (the downstream pathway) may be performed by two different microbial cells, where a first cell is genetically engineered to express one or more enzymes in the upstream pathway, and a second cell is genetically engineered to express one or more enzyme in the downstream pathway. When 5-HTP is produced using the two cell system, 5-HAA is produced by the first cell, and is taken up by the second cell as the precursor for production of the end product, 5-HTP.

The host cell is optionally further genetically engineered to further increase the amount of 5-HTP produced by the cell. Further enhancement of 5-HTP production can be achieved through a variety of methods. In one embodiment, overproduction or accumulation of 5-HTP can be achieved by knocking out one or more enzymes involved in tryptophan degradation. For example, the amount of 5-HTP produced by a cell can be increased by knocking out the gene for tryptophanase (tnaA), a protein reported to catalyze the degradation of both tryptophan and 5-HTP. In another embodiment, the trp operon is engineered to reduce or eliminate feedback inhibition. For example, a mutation at amino acid position S40, such as the mutation S40F, can incorporated into TrpE to reduce or eliminate feedback inhibition. In another embodiment, 5-HTP overproduction or accumulation can be achieved by altering expression of the tryptophan transcriptional repressor protein (TrpR). Any known method for enhancement of 5-HTP production can be used, including, for example, the methods described in U.S. Pat. No. 5,756,345. Optionally, one or more overproduction or accumulation techniques can be combined. For example, the tryptophan-degradation pathway can be knocked out, and the host cell can overexpress the entire trp operon.

The host cell is preferably a bacterial or yeast cell. Exemplary host cells include an *Escherichia coli* cell, a *Bacillus subtilis* host cell and a *Streptomyces caeruleus* cell. Exemplary yeast cells include yeasts from the genus *Saccharomyces* (e.g., *S. cerevisiae*) and the genus *Pichia*. More generally, microorganisms that can be metabolically engineered to incorporate the biosynthetic pathway described herein include *Escherichia, Salmonella, Clostridium, Zymomonas, Pseudomonas, Bacillus, Rhodococcus, Alcaligenes, Klebsiella, Paenibacillus, Lactobacillus, Enterococcus, Arthrobacter, Brevibacterium, Corynebacterium Candida, Hansenula, Pichia* and *Saccharomyces*. Preferred hosts include *Escherichia coli, Bacillus subtilis Bacillus licheniformis, Alcaligenes eutrophus, Rhodococcus erythropolis, Paenibacillus macerans, Pseudomonas putida, Enterococcus faecium, Saccharomyces cerevisiae, Lactobacillus plantarum, Enterococcus gallinarium* and *Enterococcus faecalis*. Other suitable cells can include insect cells, protists, and fungi, as well as animal or plant cells.

The invention further includes method of making the genetically engineered cell as well as methods for using the genetically engineered cell. The genetically engineered cell is cultured under conditions to produce 5-HAA and/or 5-HTP. Culturing can be small scale or large scale; it can be aerobic or anaerobic. Preferably, the genetically engineered organism is cultured in a large scale fermentation system. The 5-HAA and/or 5-HTP is separated from the microorganism and optionally isolated and purified. The resultant 5-HAA and/or 5-HTP can be further chemically or enzymatically derivatized. The 5-HAA and/or 5-HTP or there derivatives can be incorporated into other materials such as foods, supplements, medications, polymeric compounds, including heteropolymers, copolymers and the like. 5-HAA can be used as a feedstock for genetically engineered cells of the invention that express the downstream biosynthetic pathway.

Genetically engineered cells are also referred to as "metabolically engineered" cells when the genetic engineering modifies or alters one or more particular metabolic pathways so as to cause a change in metabolism. Metabolic engineering can, for example, improve the rate or conversion of a substrate into a desired product, change the amount of a product produced, or produce a new product. The present invention provides a novel metabolic pathway which synthesizes the biochemicals 5-HAA and/or 5-HTP. Methods of modifying or altering metabolic pathways in many different cell types (including bacteria, plants, and animals) are routine and well known in the art; see, e.g., Sambrook et al, *Molecular Cloning: A Laboratory Manual.*, Cold Spring Harbor Laboratory Press (1989), and *Methods for General and Molecular Bacteriology*, (eds. Gerhardt et al.) American Society for Microbiology, chapters 13-14 and 16-18 (1994).

Introduction of the Biosynthetic Pathway into a Cell

The introduction of the novel biosynthetic pathway of the invention into a cell involves expression or overexpression of one or more enzymes included in the novel biosynthetic pathway. An enzyme is "overexpressed" in a genetically engineered cell when the enzyme is expressed at a level higher than the level at which it is expressed in a comparable wild-type cell. In cells that do not express a particular endogenous enzyme, or in cells in which the enzyme is not endogenous (i.e., the enzyme is not native to the cell), any level of expression of that enzyme in the cell is deemed an "overexpression" of that enzyme for purposes of the present invention.

As will be appreciated by a person of skill in the art, overexpression of an enzyme can be achieved through a number of molecular biology techniques. For example, overexpression can be achieved by introducing into the cell one or more copies of a polynucleotide encoding the desired enzyme. The polynucleotide encoding the desired enzyme may be endogenous or heterologous to the cell. Preferably, the polynucleotide is introduced into the cell using a vector; however, naked DNA may also be used. The polynucleotide may be circular or linear, single-stranded or double stranded, and can be DNA, RNA, or any modification or combination thereof. The vector can be any molecule that may be used as a vehicle to transfer genetic material into a cell. Examples of vectors include plasmids, viral vectors, cosmids, and artificial chromosomes, without limitation. Examples of molecular biology techniques used to transfer nucleotide sequences into a microorganism include, without limitation, transfection, electroporation, transduction, and transformation. These methods are well known in the art. Insertion of a vector into a target cell is usually called transformation for bacterial cells and transfection for eukaryotic cells, however insertion of a viral vector is often called transduction. The terms transformation, transfection, and transduction, for the purpose of the instant invention, are used interchangeably herein. A polynucleotide which has been transferred into a cell via the use of a vector is often referred to as a transgene.

Preferably, the vector is an expression vector. An "expression vector" or "expression construct" is any vector that is used to introduce a specific polynucleotide into a target cell such that once the expression vector is inside the cell, the protein that is encoded by the polynucleotide is produced by the cellular transcription and translation machinery. Typically an expression vector includes regulatory sequences operably linked to the polynucleotide encoding the desired enzyme. Regulatory sequences are common knowledge to the person of the skill in the art and may include for example, an origin of replication, a promoter sequence, and/or an enhancer sequence. The polynucleotide encoding the desired enzyme can exist extrachromosomally or can be integrated into the host cell chromosomal DNA. Extrachromosomal DNA may be contained in cytoplasmic organelles, such as mitochondria (in most eukaryotes), and in chloroplasts and plastids (in plants). More typically, extrachromosomal DNA is maintained within the vector on which it was introduced into the cell. In many instances, it may be beneficial to select a high copy number vector in order to maximize the expression of the enzyme. Optionally, the vector may further contain a selectable marker. Certain selectable markers may be used to confirm that the vector is present within the target cell. Other selectable markers may be used to further confirm that the vector and/or transgene has integrated into the host cell chromosomal DNA. The use of selectable markers is common in the art and the skilled person would understand and appreciate the many uses of selectable markers. In embodiments where multiple vectors are used, it is preferred that each vector include an independent selectable marker. Optionally, the vector may further contain a reporter gene. Reporter genes may be used to confirm that the vector is expressing within the target cell, and may be further used to monitor the expression from the vector. The use of reporter genes is common in the art and the skilled person would understand and appreciate the many uses of reporter genes.

Plasmids

Enzymes that are part of the novel metabolic pathway of the invention can be expressed in the host cell from extrachromosomal elements, such as vectors. Plasmids are commonly used as expression vectors in metabolic engineering. The novel biosynthetic pathway can be conveniently expressed or overexpressed in the microbial cell through the introduction of one or more plasmids encoding the enzyme(s). Suitable exemplary plasmids are described in Example I and include but are not limited to pCS-trpDCBA, pSA-trpDCBA, pCA-trpDCBA, pCS-trpE$^{fbr}$G, pSA-trpE$^{fbr}$G, pCS-trpE$^{fbr}$G-APTA, pSA-trpE$^{fbr}$G-APTA, pZE-salABCD, pZE-salABC, and pZE-sdgC-pqsA. A person having skill in the art will appreciate that additional plasmids with different promoters, antibiotic resistance, and origins of replication (ori) can also be used.

Additionally, it should be noted that any or all of the nucleotide sequences that operably encode the enzymes described herein can instead be genomically integrated into the bacterial genome, if desired, using well-known genetic engineering techniques and protocols.

In host cells that natively express one or more of the enzymes in the biosynthetic pathway, a plasmid expressing the native enzyme is optionally omitted.

A plasmid can be a high-copy number, a medium copy-number, or a low-copy number plasmid. While the boundaries associated with the art-recognized designations "high,"

"medium" and "low" copy number are indistinct and may in practice overlap, in general a high copy number plasmid is characterized by copy numbers within a cell of, for example, greater than 50 or 60 copies, a medium copy number plasmid is characterized by copy numbers within a cell of, for example, between 10 and 60 copies (e.g., 15-20 copies), and a low copy number plasmid is characterized by copy numbers within a cell of, for example, fewer than 10 or 15 copies (e.g., 3-8 copies). Plasmids pSA-trpDCBA and pCS-trpDCBA exemplify low- and medium-copy number plasmids, respectively.

In a preferred embodiment of the method of making the genetically engineered microorganism and resultant engineered microorganism, the polynucleotides that operably encode the selected enzymes, which are engineered into the host organism, are present on one or more plasmids. A separate plasmid can be used for each enzyme, or two or more enzymes can be combined on the same plasmid. As a result, the genetically engineered host organism may include one or a plurality of plasmids to form the biosynthetic pathway (upstream, downstream or complete) for synthesis of 5-HTP or 5-HAA.

Method of Making 5-HTP

Genetically engineered cells of the invention can be grown in a medium containing a simple carbon source such as glucose or glycerol. In order to optimize cell growth and production efficiency, the cells can be incubated at a temperature, including but not limited to 21° C., 23° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 46° C. In one embodiment, the microbial cells are incubated at 30° C. In an alternative embodiment, the microbial cells are incubated at 37° C. Glucose is preferably used as carbon source for cell growth and maintenance; optionally, additional carbon sources, such as citrate, can be added to increase the titer.

Microbial production of 5-HTP may be done in a single step strategy or in a two-step strategy. In a single step strategy, the full novel biosynthetic pathway is introduced into a microbial cell to realize the de novo production of 5-HTP. For example, a microbial cell may be engineered to express trpE$^{fbr}$G, salABCD, and trpDCBA (see, for example, E. coli strail BW1 harboring plasmids pSA-trpE$^{fbr}$G, pZE-salABCD, and pCS-trpDCBA as described in Example I). However, in a single step strategy, the substrate AA is available to the tryptophan biosynthesis enzyme(s), and as a result, production of tryptophan (TP) may be favored over 5-HTP.

To solve this problem, a two-step strategy for 5-HTP production may be used. The upstream portion of the novel biosynthetic pathway is introduced into a first microbial cell, which can be cultured to produce 5-HAA. For example, the first microbial cell may be engineered to express trpE$^{fbr}$G and salABCD (see for example, E. coli strain BW3 harboring pSA-trpE$^{fbr}$G and pZE-salABCD as described in Example I) for 5-HAA production from glucose. The downstream portion of the novel biosynthetic pathway is introduced into a second microbial cell to promote conversion of 5-HAA to 5-HTP. For example, the second microbial cell may be engineered to express trpDCBA (see for example, E. coli strain BW2 harboring pSA-trpDCBA and pCA-trpDCBA as described in Example I) for 5-HTP production from 5-HAA. Advantageously, this two-step strategy interrupts TrpDBCA action on AA and avoids the shunting of carbon toward tryptophan synthesis. In a preferred embodiment, the microbial production of 5-HTP is done using a two-step strategy that includes a first microbial cell including the upstream portion of the novel biosynthetic pathway, and a second microbial cell including the downstream portion of the novel biosynthetic pathway.

Surprisingly and advantageously, it was discovered that the upstream portion of the novel biosynthetic pathway was not only able to produce 5-HAA, but the 5-HAA was secreted into the supernatant. The first microbial cells can be separated from the supernatant, and the supernatant, which contains the 5-HAA, can be mixed with the second microbial cell culture, thereby providing the raw material for synthesis of 5-HTP. In an alternative embodiment, the first and second microbial cells are co-cultured. Thus, in one embodiment, the first and second microbial cells are cultured sequentially, and in another embodiment, the first and second microbial cells are co-cultured.

The simple carbon source may be any readily available carbon source. Suitable carbon sources may include, without limitation, 5-carbon sugars or 6-carbon sugars. Non-limiting examples of 5-carbon sugars include, without limitation, xylose and arabinose. Non-limiting examples of 6-carbon sugars include, without limitation, glucose, glycerol, mannose, galactose, and sorbose. In one embodiment, the simple carbon source is glucose.

Optionally, 5-HTP is isolated from the cell that includes the downstream portion of the metabolic pathway, or the full pathway. The 5-HTP can be isolated from the cell supernatant, if the compound is excreted, or from the cell itself. The isolated 5-HTP is optionally purified. The purified 5-HTP may be used as the starting material for other chemical or enzymatic reactions to produce other biochemicals of interest. Likewise, the intermediate metabolite 5-HAA can be isolated and optionally purified from a cell that includes only the upstream portion of the pathway or from the cell supernatant if the 5-HAA is excreted. The intermediate metabolite can be used as a feedstock for the production of 5-HTP according to the invention, or for other applications in metabolic engineering or as a precursor for the enzymatic chemical synthesis of other products.

Optionally, the isolated 5-HTP is incorporated into a food product as a food additive, food supplement, or nutraceutical. For example, the isolated 5-HTP can be incorporated into an animal feed, such as feed for domestic or farm animals. Supplementation with 5-HTP can have beneficial effects relating to calcium metabolism and is especially suitable for pregnant and lactating farm animals such as cows. The method of making 5-HTP therefore optionally includes packaging and/or marketing the 5-HTP as an animal food supplement, additive or nutraceutical, as well as incorporating the 5-HTP into a food product such as an animal feed or beverage.

The genetically engineered cells of the invention can be utilized as probiotic. As a probiotic, the cells, which may contain the upstream metabolic pathway, the downstream metabolic pathway, or both, as described herein, may be administered in supplement form or they may be incorporated into a food product. Optionally, the food product is a fermented or cultured food product. Exemplary food products include dairy products, such as milk, cheese, or yoghurt. *Lactobacillus* and *Bacillus* are exemplary bacterial cells for use as a probiotic.

EXAMPLES

The present invention is illustrated by the following examples. It is to be understood that the particular examples, materials, amounts, and procedures are to be interpreted broadly in accordance with the scope and spirit of the invention as set forth herein.

Example I

Precursor-Directed Biosynthesis of 5-Hydroxytryptophan Using Metabolically Engineered E. coli A novel biosynthetic pathway was designed and verified reversely leading to the production of 5-hydroxytryptophan (5-HTP) from glucose. This pathway takes advantage of the relaxed substrate selectivities of relevant enzymes without employing the unstable tryptophan 5-hydroxylase. A high-titer of 5-HTP was produced from a 5-hydroxyanthranilate (5-HAA) precursor by the catalysis of E. coli TrpDCBA. A novel salicylate 5-hydroxylase was used to convert the non-natural substrate anthranilate (AA) to 5-HAA, and production of 5-HAA from glucose was enhanced using modular optimization. In the end, we combined the full pathway by adopting a two-stage strategy to realize the de novo production of 5-HTP. The strategy and concept used in this study will benefit the design and establishment of non-natural pathways for the biosynthesis of other chemicals.

Results

5-Hydroxytryptophan (5-HTP) is a natural non-proteinogenic amino acid and serves as a direct biosynthetic precursor to the neurotransmitter serotonin. 5-HTP has been shown to be effective for the treatment of a variety of conditions, including depression, insomnia, chronic headaches and binge eating associated with obesity. The therapeutic efficacy of 5-HTP is due to its ability to enhance the synthesis of serotonin in the brain. 5-HTP is well absorbed from an oral dose and can easily cross the blood-brain barrier[1].

Currently, extraction from the seeds of African plant Griffonia simplicifolia is the approach for 5HTP commercial production. However, the material supply is seasonally and regionally dependent, which limits the output of 5-HTP. Although chemical synthesis of 5-HTP has been reported[2], it is not economically feasible in large scale. Biosynthesis provides a promising alternative to 5-HTP production. Microorganisms have simpler genetic backgrounds and metabolic networks. They grow faster and the biomass can reach high levels in simple synthetic medium. Many important chemicals have been successfully produced using genetically engineered microorganisms[3-12].

So far, the only reported 5-HTP biosynthetic pathway is via tryptophan, and the reaction is catalyzed by tryptophan 5-hydroxylase (T5H). However, T5H is unstable when expressed in microorganisms and requires a special co-factor 5,6,7,8-tetrahydrobiopterin (BH4) that should be regenerated by additional enzyme reactions[13]. These problems hampered the application of this pathway to the economical production of 5-HTP. To circumvent these problems, we established a novel artificial pathway for 5-HTP biosynthesis. This pathway takes the advantage of the substrate tolerance of the pathway enzymes and implements the concept of precursor-directed biosynthesis (FIG. 1).

The first step of the pathway design (Step 1 of FIG. 1, farthest downstream) is to find a simple precursor to 5-HTP. In E. coli tryptophan biosynthetic pathway, anthranilate (AA) is a precursor of tryptophan and it is converted into tryptophan via five enzymatic reactions, which are catalyzed by TrpDCBA. 5-HTP is an analogue of tryptophan and its corresponding precursor should be 5-hydroxyanthranilate (5-HAA). It has been reported that substituted AA can also be converted into the corresponding substituted tryptophan through the pathway[14]. To investigate the reaction details, a medium-copy-number plasmid pCS-trpDCBA was constructed. E. coli strain BW2 with the knockouts of tnaA and trpE harboring pCS-trpDCBA was used for the in vivo assay. The knockout of tnaA can prevent the products tryptophan and 5-HTP from degradation while the knockout of trpE can block the native synthesis of AA.

The results showed that AA and 5-HAA can both go through these pathway enzymes, producing tryptophan and 5-HTP, respectively. The in vivo specific activity of the bioconversion system towards 5-HAA (57.44±0.94 µM/OD/h) is about 40% of that towards AA (151.37±2.93 µM/OD/h), which indicated that the 5-hydroxyl group affected the enzyme activities to some extent (FIG. 2). We also cloned trpDCBA into a low-copy-number plasmid yielding pSA-trpDCBA. Interestingly, when strain BW2 harboring pSA-trpDCBA was used for the in vivo assays, the intermediate 5-hydroxyindole (5-HI) was accumulated in the cultures, indicating that the reaction catalyzed by TrpB was a rate-limiting step (FIG. 3A). To test the capacity of this partial pathway, we continuously fed 5-HAA to the cultures of BW2 harboring pCS-trpDCBA. In 12 h, 1102.43±24.95 mg/L of 5-HTP was produced (FIG. 3B).

The second step of 5-HTP biosynthesis (Step 2 in FIG. 1) is to synthesize 5-HAA from a primary metabolite. AA is a potential precursor of 5-HAA since the 5-hydroxylation of AA will lead to the formation of 5-HAA. However, there were no AA 5-hydroxylases reported so far. Notably, two salicylate 5-hydroxylases (S5Hs) had been characterized from Ralstonia sp. Strain U2 and Pseudomonas aeruginosa Strain JB2[15, 16]. S5H hydroxylates salicylate into gentisate (GA) and is involved in the degradation of aromatic compounds. Since salicylate (2-hydroxybenzoate) and AA (2-aminobenzoate) have very similar molecular structures, we hypothesized that S5H may also hydroxylate AA. To test this hypothesis, we searched the protein database and found a gene cluster encoding a putative S5H. The cluster was cloned from Ralstonia eutropha H16 and designated as salABCD. Unlike the former two S5Hs, this cluster locates on the chromosome rather than on a mobile plasmid. While SalABC showed high protein sequence similarity with those from Ralstonia sp. Strain U2 (57%-75%), SalD showed only 13% similarity with that from Ralstonia sp. Strain U2.

To characterize the gene cluster and test the necessity of SalD, we constructed two high-copy-number plasmids pZE-salABCD and pZE-salABC. E. coli strain BW3 with the knockouts of tnaA and trpD was transformed with these two plasmids, separately. The knockout of trpD can block the consumption of AA and 5-HAA by the native TrpDCBA.

The in vivo assay showed that SalABCD can convert salicylate into GA with a specific activity of 268.72±7.79 µM/OD/h. We then further tested the enzyme activity towards AA. As expected, the enzyme system could also convert AA into 5-HAA, although with a slightly lower specific activity (216.06±2.02 µM/OD/h). However, the specific activity of SalABC towards AA decreased significantly to 16.75±2.06 µM/OD/h, which proved that SalD is an essential component of the S5H (FIG. 4). It is worth mentioning here that SalABCD requires NAD(P)H as the co-factor instead of BH4 and the former ones are abundant metabolites in E. coli.

We also tested another enzyme combination to hydroxylate AA, which consisted of an anthraniloyl-CoA synthetase (PqsA) and a salicyloyl-CoA 5-hydroxylase (SdgC). PqsA is involved in the biosynthesis of 2,4-dihydroxyquinoline, an extracellular metabolite produced by *Pseudomonas aeruginosa*[17]. SdgC takes part in salicylate degradation by *Streptomyces* sp. strain WA46[18]. The in vivo assay showed that AA could be converted into 5-HAA by the sequential catalyzation of these two enzymes. However, compared with that of SalABCD, the specific activity of this combination is not desirable (15.44±0.92 μM/OD/h) (FIG. 4). We then continuously fed AA to the cultures of strain BW3 harboring plasmid pZE-salABCD. In 12 h, 442.51±6.25 mg/L 5-HAA was produced (FIG. 5).

The last step (Step 3 in FIG. 1, farthest upstream) to establish the 5-HTP biosynthesis is to connect the non-native downstream partial pathway with the *E. coli* native metabolism. As the production of AA in *E. coli* had been reported in our previous work[19], here we optimized the production of 5-HAA from glucose by combining the AA production and conversion partial pathways. The 5-HAA biosynthetic pathway was divided into three modules (FIG. 1). Module 1 consists of salABCD, which catalyzes the formation of 5-HAA from AA; module 2 is the trpE$^{fbr}$G module, which converts chorismate to AA; and module 3 is the APTA module, which expresses four enzymes (AroL, PpsA, TktA, AroG$^{fbr}$) in the shikimate pathway to boost the carbon flux towards chorismate synthesis.

Modular optimization results showed that the highest titer (224.31±8.89 mg/L) of 5-HAA was obtained when module 1 was in high-copy-number plasmid (pZE-salABCD) and module 2 in low-copy-number plasmid (pSA-trpE$^{fbr}$G) (FIG. 6). The introduction of module 3 did not further improve the titer. In addition, the intermediate AA was accumulated in all cases, which indicated that module 1 was still a rate-limiting step, even expressed by the high-copy-number plasmid.

After achieving the production of 5-HAA from glucose, we tried to combine the full pathway to realize the de novo production of 5-HTP. *E. coli* strain BW1 with the knockout of tnaA was transformed with plasmids pSA-trpE$^{fbr}$G, pZE-salABCD and pCS-trpDCBA. The positive transformants were used for shake flask experiments. To our surprise, after 24 h of cultivation no 5-HTP was accumulated in the cultures; while tryptophan was produced at 205.14±6.71 mg/L. One explanation for this phenomenon is that TrpD-CBA showed higher substrate affinity and specific activity towards AA than 5HAA and AA was directly converted to tryptophan without being hydroxylated. Another possible reason is that TrpE and TrpD have been evolved to form heterotetrameric complex to decrease substrate diffusion[20]. The formation of this enzyme complex may prevent SalABCD from getting access to its substrate AA.

To solve this problem, we then developed a two-step strategy for 5-HTP production. First, *E. coli* strain BW3 harboring pSA-trpE$^{fbr}$G and pZE-salABCD was used for 5-HAA production from glucose. After 24 h, the cells were removed by centrifugation and the supernatants were mixed with equal volume of the cultures of *E. coli* strain BW2 harboring pSA-trpDCBA and pCA-trpDCBA. Plasmid pCA-trpDCBA was constructed by replacing the kanamycin resistance gene of plasmid pCS-trpDCBA with ampicillin resistance gene. The produced 5-HAA was further converted into 5-HTP and the final titers can reach 98.09±3.24 mg/L (FIG. 7). In addition, 23.05±0.83 mg/L tryptophan was also produced as the by-product and the accumulation of the intermediate 5-HI was not observed.

Methods

Strains, Plasmids and Medium.

Strains and plasmids are summarized in Table 1 and 2, respectively. *E. coli* strain XL1-Blue was used as the host for standard cloning and plasmid propagation. *E. coli* strains BW1, BW2, BW3 were used for in vivo assays and the production of 5-HAA and 5-HTP. Luria-Bertani (LB) medium was used for inoculant preparation and cell propagation. Modified M9 medium was used for microbial synthesis of 5-HAA and 5-HTP. LB medium contains 10 g/L tryptone, 5 g/L yeast extract and 10 g/L NaCl. The modified M9 minimal medium contains 10 g/L glucose, 6 g/L Na$_2$HPO$_4$, 0.5 g/L NaCl, 3 g/L KH$_2$PO$_4$, 1 g/L NH$_4$Cl, 1 mM MgSO$_4$, 0.1 mM CaCl$_2$, 2 g/L yeast extract, 2 g/L sodium citrate and 100 mg/L serine. When needed, ampicillin, kanamycin, chloramphenicol were added to the medium at 100 μg/mL, 50 μg/mL, 34 μg/mL, respectively.

TABLE 1

Strains used in this study.

| Strains | Genotype | Source |
|---|---|---|
| XL1-Blue | recA1 endA1 gyrA96 thi-1 hsdR17 supE44 relA1 lac [F' proAB lacI$^q$ZΔM15 Tn10 (Tet$^r$)] | Stratagene |
| BW25113 ΔtnaA::kan | F-, Δ(araD-araB)567, ΔlacZ4787(::rrnB-3), λ⁻, rph-1, ΔtnaA739::kan, Δ(rhaD-rhaB)568, hsdR514 | CGSC* |
| BW1 | BW25113ΔtnaA, Δkan | This study |
| BW2 | BW1ΔtrpE | This study |
| BW3 | BW1ΔtrpD | This study |

CGSC*: Coli Genetic Stock Center

Plasmids Construction.

Plasmids pZE12-luc, pCS27, pSA74 were employed for gene cloning, protein expression, and pathway assembly (Lin et al., 2013 Nat. Commun. 4:2603). The genes salAB and salCD were amplified from *Ralstonia eutropha* genomic DNA. The genes pqsA and sdgC were amplified from *Pseudomonas aeruginosa* and *Streptomyces* sp. Strain WA46 genomic DNAs, respectively. The genes trpDCBA were amplified from *E. coli* genomic DNA. Plasmid pZE-salABCD was constructed by subcloning salAB and salCD into plasmid pZE12-luc using KpnI, BamHI and XbaI. Plasmid pZE-salABC was constructed using the same strategy. Plasmid pZE-sdgC-pqsA was constructed by inserting the fragments of sdgC and pqsA into pZE12-luc using KpnI, NdeI and SphI. Plasmid pCS-trpE$^{fbr}$G was constructed in our previous study (Sun et al., 2013 Appl. Environ. Microbiol. 79:4024-4030). pSA-trpE$^{fbr}$G was constructed by subcloning trpE$^{fbr}$G into plasmid pSA74 using KpnI and BamHI. Plasmids pCS-trpDCBA and pSA-trpDCBA were constructed by inserting the trpDCBA genes into pCS27 and pSA74 using KpnI and BamHI. Plasmid pCA-trpDCBA was constructed by replacing the kanamycin resistance marker of pCS-trpDCBA with the ampicillin resistance marker. Plasmid pCS-APTA was constructed in our previous study (Lin et al., 2013, Nat. Commun. 4:2603). The expression cassette P$_L$lacO1-APTA was PCR amplified and inserted into plasmid pCS-trpE$^{fbr}$G and pSA-trpE$^{fbr}$G using SacI and SpeI, yielding plasmids pCS-trpE$^{fbr}$G-APTA and pSA-trpE$^{fbr}$G-APTA, respectively.

TABLE 2

Plasmids used in this study.

| Plasmids | Description | Source/Reference |
|---|---|---|
| pZE12-luc | P$_L$lacO1, colE ori, luc, Amp$^r$ | a |
| pCS27 | P$_L$lacO1, P15A ori, Kan$^r$ | a |

TABLE 2-continued

Plasmids used in this study.

| Plasmids | Description | Source/Reference |
|---|---|---|
| pSA74 | P$_L$lacO1, pSC101 ori, Cm$^r$ | a |
| pCS-trpDCBA | pCS27, trpDCBA from E. coli | This study |
| pSA-trpDCBA | pSA74, trpDCBA from E. coli | This study |
| pCA-trpDCBA | pCA27, trpDCBA from E. coli | This study |
| pCS-trpE$^{fbr}$G | pCS27, trpE$^{fbr}$ G from E. coli | b |
| pSA-trpE$^{fbr}$G | pSA74, trpE$^{fbr}$ G from E. coli | This study |
| pCS-trpE$^{fbr}$G-APTA | pCS27, trpE$^{fbr}$ G, aroL, ppsA, tktA, aroG$^{fbr}$ from E. coli, two operons | This study |
| pSA-trpE$^{fbr}$G-APTA | pSA74, trpE$^{fbr}$ G, aroL, ppsA, tktA, aroG$^{fbr}$ from E. coli, two operons | This study |
| pZE-salABCD | pZE12-luc, salAB and salCD from R. eutropha | This study |
| pZE-salABC | pZE12-luc, salAB and salC from R. eutropha | This study |
| pZE-sdgC-pqsA | pZE12-luc, sdgC from Streptomyces sp. Strain WA46 and pqsA from P. aeruginosa | This study | a. Lin et al, 2013, Nat. Commun. 4: 2603
b. Sun et al., 2013 Appl. Environ .Microbiol. 79: 4024-4030

In Vivo Enzyme Assays.

In vivo assays were carried out to evaluate the activities of TrpDCBA and anthranilate 5-hydroxylases towards their substrates. E. coli BW25113 derivative strains were transformed with the corresponding plasmids. Fresh colonies were inoculated into 3 mL LB medium containing appropriate antibiotics and grown aerobically at 37° C. Overnight cultures were inoculated into 20 mL LB medium and left to grow at 37° C. When OD$_{600}$ reached 0.4, the cultures were induced with 0.25 mM IPTG at 30° C. for 3 h. Cells were then harvested by centrifugation, and re-suspended in the modified M9 medium. The cell suspensions were fed with the corresponding substrates and incubated at 30° C. with shaking Samples were taken after 1 h and the product concentrations were detected by HPLC. The specific activity was expressed as μM/OD/h. For the bioconversion experiments, substrates were added to the cell suspensions at several time points. Samples were taken every few hours and used for the analysis of the cell growth and product accumulation.

Microbial Production of 5-HAA.

E. coli strain BW3 was transformed with the corresponding plasmids. Overnight cultures were inoculated into the modified M9 medium containing appropriate antibiotics and cultivated at 30° C. with shaking. When OD$_{600}$ reached 0.4, the cultures were induced with 0.25 mM IPTG and continued to grow at 30° C. Samples were taken every few hours. OD$_{600}$ values were measured and the product 5-HAA and the intermediates were analyzed by HPLC.

Microbial Production of 5-HTP.

We tried two different strategies for the production of 5-HTP from glucose. In the first strategy, E. coli strain BW1 was transformed with plasmids pZE-salABCD, pSA-trpE$^{fbr}$G and pCS-trpDCBA. Overnight cultures were inoculated into 20 mL modified M9 medium containing ampicillin, kanamycin, chloramphenicol and left to grow at 30° C. When OD$_{600}$ reached 0.4, the cultures were induced with 0.25 mM IPTG. Samples were taken and the product and the intermediates were analyzed by HPLC. The second strategy was a two-stage process. First, E. coli strain BW3 was transformed with plasmids pZE-salABCD and pSA-trpE$^{fbr}$G. Overnight cultures were inoculated into 20 mL modified M9 medium containing ampicillin, chloramphenicol and left to grow at 30° C. When OD$_{600}$ reached 0.4, the cultures were induced with 0.25 mM IPTG. After 24 h of cultivation, the cultures were harvested by centrifugation and the supernatant was mixed with equal volume of the cultures of strain BW2 harboring pCA-trpDCBA and pSA-trpDCBA, which had already been induced with 0.25 mM IPTG for 3 h. The new cultures continued to be cultivated at 30° C. with shaking Samples were taken every 4 hours, and the substrate consumption and the product and intermediate accumulation were detected by HPLC.

HPLC Analysis.

Salicylate, GA, AA, 5-HAA, tryptophan, 5-HTP, 5-HI were purchased from Sigma Aldrich or Acros Organics and were used as the standards. Both the standards and samples were analyzed and quantified by HPLC (Dionex Ultimate 3000) equipped with a reverse phase ZORBAX SB-C18 column and an Ultimate 3000 Photodiode Array Detector. Solvent A was water with 0.2% trifluoroacetic acid, and solvent B was methanol. The column temperature was set to 28° C. The following gradient was used at a flow rate of 1 ml/min: 5 to 50% solvent B for 15 min, 50 to 5% solvent B for 1 min, and 5% solvent B for an additional 4 min. Quantification of each compound was based on the peak areas at absorbance of specific wavelengths (salicylate 303 nm, GA 331 nm, AA 330 nm, 5-HAA 297 nm, tryptophan 275 nm, 5-HTP 276 nm, 5-HI 271 nm).

REFERENCES

1. Birdsall, T. C. (1998) 5-Hydroxytryptophan: a clinically-effective serotonin precursor. Ahern. Med. Rev. 3, 271-280.
2. Frangatos, G., and Chubb, F. L. (1959) A new synthesis of 5-hydroxytryptophan. Can. J. Chem. 37, 1374-1376.
3. Lin, Y., Shen, X., Yuan, Q., and Yan, Y. (2013) Microbial biosynthesis of the anticoagulant precursor 4-hydroxycoumarin. Nat. Commun. 4, 2603.
4. Zhang, K., Sawaya, M. R., Eisenberg, D. S., and Liao, J. C. (2008) Expanding metabolism for biosynthesis of nonnatural alcohols. Proc. Natl. Acad. Sci. U.S.A 105, 20653-20658.
5. Westfall, P. J., Pitera, D. J., Lenihan, J. R., Eng, D., Woolard, F. X., Regentin, R., Horning, T., Tsuruta, H., Melis, D. J., Owens, A., Fickes, S., Diola, D., Benjamin, K. R., Keasling, J. D., Leavell, M. D., McPhee, D. J., Renninger, N. S., Newman, J. D., and Paddon, C. J. (2012) Production of amorphadiene in yeast, and its conversion to dihydroartemisinic acid, precursor to the antimalarial agent artemisinin. Proc. Natl. Acad. Sci. U.S.A 109, E111-118.
6. Xu, P., Gu, Q., Wang, W., Wong, L., Bower, A. G., Collins, C. H., and Koffas, M. A. (2013) Modular optimization of multi-gene pathways for fatty acids production in E. coli. Nat. Commun. 4, 1409.
7. Lin, Y., Sun, X., Yuan, Q., and Yan, Y. (2013) Combinatorial biosynthesis of plant-specific coumarins in bacteria. Metab. Eng. 18, 69-77.
8. Huang, Q., Lin, Y., and Yan, Y. (2013) Caffeic acid production enhancement by engineering a phenylalanine over-producing Escherichia coli strain. Biotechnol. Bioeng. 110, 3188-3196.
9. Ajikumar, P. K., Xiao, W. H., Tyo, K. E., Wang, Y., Simeon, F., Leonard, E., Mucha, O., Phon, T. H., Pfeifer, B., and Stephanopoulos, G. (2010) Isoprenoid pathway optimization for Taxol precursor overproduction in Escherichia coli. Science 330, 70-74.

10. Atsumi, S., Hanai, T., and Liao, J. C. (2008) Non-fermentative pathways for synthesis of branched-chain higher alcohols as biofuels. Nature 451, 86-89.
11. Lin, Y., Sun, X., Yuan, Q., and Yan, Y. (2014) Extending shikimate pathway for the production of muconic acid and its precursor salicylic acid in Escherichia coli. Metab. Eng. 23, 62-69.
12. Lin, Y., and Yan, Y. (2014) Biotechnological production of plant-specific hydroxylated phenylpropanoids. Biotechnol. Bioeng. 111, 1895-1899.
13. Hamdan, F. F., and Ribeiro, P. (1999) Characterization of a stable form of tryptophan hydroxylase from the human parasite Schistosoma mansoni. J. Biol. Chem. 274, 21746-21754.
14. Chase, M. W., Power, S. D., and Whited, G. M. (1995) Microbial production of 4-, 5-, 6- and 7-substituted indole and tryptophan analogs via fermentation, WO 1995/034657, published Dec. 21, 1995.
15. Zhou, N. Y., Al-Dulayymi, J., Baird, M. S., and Williams, P. A. (2002) Salicylate 5-hydroxylase from Ralstonia sp. strain U2: a monooxygenase with close relationships to and shared electron transport proteins with naphthalene dioxygenase. J. Bacteriol. 184, 1547-1555.
16. Hickey, W. J., Sabat, G., Yuroff, A. S., Arment, A. R., and Perez-Lesher, J. (2001) Cloning, nucleotide sequencing, and functional analysis of a novel, mobile cluster of biodegradation genes from Pseudomonas aeruginosa strain JB2. Appl. Environ. Microbiol. 67, 4603-4609.
17. Zhang, Y. M., Frank, M. W., Zhu, K., Mayasundari, A., and Rock, C. O. (2008) PqsD is responsible for the synthesis of 2,4-dihydroxyquinoline, an extracellular metabolite produced by Pseudomonas aeruginosa. J. Biol. Chem. 283, 28788-28794.
18. Ishiyama, D., Vujaklija, D., and Davies, J. (2004) Novel pathway of salicylate degradation by Streptomyces sp. strain WA46. Appl. Environ. Microbiol. 70, 1297-1306.
19. Sun, X., Lin, Y., Huang, Q., Yuan, Q., and Yan, Y. (2013) A novel muconic acid biosynthesis approach by shunting tryptophan biosynthesis via anthranilate. Appl. Environ. Microbiol. 79, 4024-4030.
20. Balderas-Hernandez, V. E., Sabido-Ramos, A., Silva, P., Cabrera-Valladares, N., Hernandez-Chavez, G., Baez-Viveros, J. L., Martinez, A., Bolivar, F., and Gosset, G. (2009) Metabolic engineering for improving anthranilate synthesis from glucose in Escherichia coli. Microb. Cell Fact. 8, 19.

The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

In the event that any inconsistency exists between the disclosure of the present application and the disclosure(s) of any document incorporated herein by reference, the disclosure of the present application shall govern.

All headings are for the convenience of the reader and should not be used to limit the meaning of the text that follows the heading, unless so specified.

The complete disclosures of all patents, patent applications including provisional patent applications, publications including patent publications and nonpatent publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference.

What is claimed is:

1. A microbial system for the production of 5-hydroxytryptophan (5-HTP) comprising a plurality of genetically engineered cells comprising:
   a first genetically engineered cell comprising (i) at least one shikimate pathway enzyme, (ii) at least one enzyme having anthranilate synthase activity, and (iii) at least one enzyme having salicylate 5-hydroxylase (S5H) activity, which enzyme further has activity toward anthranilate (AA); and
   a second genetically engineered cell comprising at least one enzyme having tryptophan biosynthesis activity, wherein the enzyme catalyzes the conversion of anthranilate (AA) to tryptophan and further has activity toward 5-hydroxyanthranilate (5-HAA).

2. The microbial system of claim 1 wherein the enzyme having salicylate 5-hydroxylase (S5H) activity catalyzes the 5-hydroxylation of AA to yield 5-hydroxyanthranilate (5-HAA).

3. The microbial system of claim 1 wherein the enzyme having tryptophan biosynthesis activity catalyzes the conversion of 5-HAA to 5-HTP.

4. The microbial system of claim 1 wherein the at least one shikimate pathway enzyme comprises a shikimate kinase, a phosphoenolpyruvate synthase, a transketolase, and a 3-deoxy-D-arabinoheptulosonate 7-phosphate (DAHP) synthase.

5. The microbial system of claim 4 wherein the first cell comprises a plurality of Escherichia coli shikimate pathway enzymes.

6. The microbial system of claim 1 wherein the enzyme having anthranilate synthase activity comprises an E. coli TrpEG.

7. The microbial system of claim 1 wherein the enzyme having anthranilate synthase activity comprises a feedback inhibition mutant enzyme encoded by trpE$^{fbr}$G present in a low-copy-number plasmid.

8. The microbial system of claim 1 wherein the enzyme having salicylate 5-hydroxylase (S5H) activity comprises a R. eutropha H16 salicylate 5-hydroxylase.

9. The microbial system of claim 1 wherein the first genetically engineered cell comprises at least one vector operably encoding at least one of a shikimate pathway enzyme, an enzyme having anthranilate synthase activity, and an enzyme having salicylate 5-hydroxylase (S5H) activity.

10. The microbial system of claim 9 wherein the first genetically engineered cell comprises a plurality of vectors, wherein each of the plurality of vectors operably encodes at least one of a shikimate pathway enzyme, an enzyme having anthranilate synthase activity, and an enzyme having salicylate 5-hydroxylase (S5H) activity.

11. The microbial system of claim 10 wherein the first genetically engineered cell comprises a first vector operably encoding a shikimate pathway enzyme, a second vector operably encoding an enzyme having anthranilate synthase activity, and a third vector operably encoding an enzyme having salicylate 5-hydroxylase (S5H) activity.

12. The microbial system of claim 1 wherein the first genetically engineered cell comprises a high copy number plasmid operably encoding an enzyme having salicylate 5-hydroxylase (S5H) activity.

13. The microbial system of claim 1 wherein the first genetically engineered cell comprises a low copy number plasmid operably encoding an enzyme having anthranilate synthase activity.

14. The microbial system of claim 1 wherein the first genetically engineered cell comprises a plasmid operably encoding a shikimate kinase, a phosphoenolpyruvate synthase, a transketolase, and a DAHP synthase.

15. The microbial system claim 1 wherein the enzyme having tryptophan biosynthesis activity comprises an *E. coli* TrpDCBA.

16. The microbial system of claim 1 wherein the first and second cells are bacterial cells.

17. The microbial system of claim 1 wherein the first and second cells are *Escherichia coli* cells.

18. The microbial system of claim 1 wherein at least one enzyme is heterologous to the first or second cell.

19. The microbial system of claim 1 wherein at least one enzyme is naturally occurring in the first or second cell.

20. The microbial system of claim 1 wherein the first cell is genetically engineered to reduce or eliminate feedback inhibition of chorismate biosynthesis, anthranilate biosynthesis or both.

21. The microbial system of claim 1 wherein the first cell is genetically engineered to redirect carbon flow toward chorismate biosynthesis, anthranilate biosynthesis, or both.

22. A genetically engineered cell comprising
at least one shikimate pathway enzyme;
a vector operably encoding at least one enzyme having anthranilate synthase activity; and
a vector operably encoding at least one enzyme having salicylate 5-hydroxylase (S5H) activity, which enzyme further has activity toward anthranilate (AA).

23. A method for making 5-hydroxytryptophan (5-HTP) comprising:
culturing a first genetically engineered cell comprising (i) at least one shikimate pathway enzyme, (ii) at least one enzyme having anthranilate synthase activity, and (iii) at least one enzyme having salicylate 5-hydroxylase (S5H) activity, which enzyme further has activity toward anthranilate (AA), under conditions and for a time sufficient to produce 5-HAA; and
culturing a second genetically engineered cell comprising at least one enzyme having tryptophan biosynthesis activity, wherein the enzyme catalyzes the conversion of anthranilate (AA) to tryptophan and further has activity toward 5-hydroxyanthranilate (5-HAA), in the presence of the 5-HAA under conditions and for a time sufficient to produce 5-HTP.

24. The method of claim 23 further comprising, prior to culturing the second cell with the 5-HAA, separating the first cell from the 5-HAA.

25. The method of claim 23 wherein culturing the first cell produces a supernatant comprising the 5-HAA.

26. The method of claim 23 wherein the first and second cells are cultured simultaneously in a co-culture.

27. The method of claim 23 wherein the first cell is cultured in the presence of glucose.

28. The method of claim 23 further comprising isolating the 5-HTP.

* * * * *

UNITED STATES PATENT AND TRADEMARK OFFICE
CERTIFICATE OF CORRECTION

PATENT NO. : 9,663,768 B2
APPLICATION NO. : 14/809712
DATED : May 30, 2017
INVENTOR(S) : Yan et al.

Page 1 of 1

It is certified that error appears in the above-identified patent and that said Letters Patent is hereby corrected as shown below:

In the Claims

Column 23, Line 25: 'system claim 1' should read --system of claim 1--

Signed and Sealed this
Fifteenth Day of January, 2019

Andrei Iancu
*Director of the United States Patent and Trademark Office*